US010799578B2

(12) United States Patent
Bucklin et al.

(10) Patent No.: US 10,799,578 B2
(45) **Date of Patent: *Oct. 13, 2020**

(54) VACCINE AGAINST PORCINE PARVOVIRUS

(71) Applicant: Boehringer Ingelheim Vetmedica GmbH, Ingelheim am Rhein (DE)

(72) Inventors: Scott Eugene Bucklin, Osage Beach, MO (US); Troy James Kaiser, Dearborn, MO (US); Jeremy Kroll, Urbandale, IA (US); Philip Utley, Slater, IA (US); Eric Martin Vaughn, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/598,110

(22) Filed: Oct. 10, 2019

(65) Prior Publication Data

US 2020/0030438 A1 Jan. 30, 2020

Related U.S. Application Data

(63) Continuation of application No. 15/801,730, filed on Nov. 2, 2017, now Pat. No. 10,485,866.

(30) Foreign Application Priority Data

Nov. 3, 2016 (EP) .................................... 16197091

(51) Int. Cl.

| | |
|---|---|
| *A61K 39/23* | (2006.01) |
| *A61K 39/12* | (2006.01) |
| *C07K 14/005* | (2006.01) |
| *A61P 31/20* | (2006.01) |
| *C12N 7/00* | (2006.01) |
| *A61K 39/00* | (2006.01) |

(52) U.S. Cl.
CPC .............. *A61K 39/23* (2013.01); *A61K 39/12* (2013.01); *A61P 31/20* (2018.01); *C07K 14/005* (2013.01); *C12N 7/00* (2013.01); *A61K 2039/552* (2013.01); *C12N 2750/14322* (2013.01); *C12N 2750/14323* (2013.01); *C12N 2750/14334* (2013.01); *C12N 2750/14371* (2013.01); *C12N 2770/10034* (2013.01)

(58) Field of Classification Search
None
See application file for complete search history.

(56) References Cited

U.S. PATENT DOCUMENTS

| | | | | |
|---|---|---|---|---|
| 5,498,413 | A | 3/1996 | Casal Alvarez et al. | |
| 7,109,025 | B1 * | 9/2006 | Eloit ...................... | C12N 15/86 435/320.1 |
| 10,485,866 | B2 * | 11/2019 | Bucklin .................. | C12N 7/00 |
| 2012/0164170 | A1 | 6/2012 | Kuo et al. | |
| 2014/0170180 | A1 | 6/2014 | Iyer et al. | |
| 2014/0234354 | A1 | 8/2014 | Iyer et al. | |
| 2015/0246113 | A1 | 9/2015 | Iyer et al. | |
| 2015/0283230 | A1 | 10/2015 | Iyer et al. | |
| 2020/0030438 | A1 * | 1/2020 | Bucklin ............... | C07K 14/005 |

FOREIGN PATENT DOCUMENTS

| | | | |
|---|---|---|---|
| CN | 102488895 | A | 6/2012 |
| CN | 102727881 | A | 10/2012 |
| CN | 104288760 | A | 1/2015 |
| EP | 0117767 | A1 | 9/1984 |
| EP | 0551449 | A1 | 7/1993 |
| RU | 2004108484 | A | 9/2005 |
| WO | 198802026 | A1 | 3/1988 |
| WO | 2011107534 | A1 | 9/2011 |
| WO | 2014099669 | A1 | 6/2014 |
| WO | 2014127084 | A1 | 8/2014 |

OTHER PUBLICATIONS

Cui, J., et al. "Genome sequence of Chinese porcine parvovirus strain PPV2010." Journal of virology 86.4 (2012): 2379-2379.
Database UniProt Accession No. K4K2G7, Jan. 9, 2013, Retrieved from EBI accession No. UniProt: K4K2G7, pp. 1-3.
Database UniProt Accession No. K4K4H5, Jan. 9, 2013, Retrieved from EBI accession No. UniProt: K4K4H5, pp. 1-3.
Database UniProt Accession No. Q32Z58, Dec. 6, 2005, Retrieved from EBI accession No. UniProt: Q32Z58, pp. 1-3.
GenBank Accession No. JX896318, Xiao et al., "Identification of a new porcine parvovirus: an evidence for the coexistence of different intermediates during the evolution of parvovirus". College of Veterinary Medicine, Iowa State University, Department of Veterinary Diagnostic and Production Animal Medicine, Oct. 2012, pp. 1-4.
GenBank Accession No. JX896320.1, Xiao et al., "Complete Genome Sequence of a Novel Porcine Parvovirus (PPV) Provisionally Designated PPV5". Genome Announcement, vol. 1, No. 1, E00021-12, 2012, pp. 1-3.

(Continued)

*Primary Examiner* — Shanon A. Foley
(74) *Attorney, Agent, or Firm* — Richard Seeger; John Ezcurra

(57) ABSTRACT

The present invention relates to a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue. Further, the present invention relates to immunogenic compositions comprising said PPV viral protein 2 (VP2). Furthermore, the present invention relates to methods for immunizing a subject comprising administering to such subject the immunogenic composition of the present invention. Moreover, the present invention relates to methods of treating or preventing clinical signs caused by PPV infection in a subject of need, the method comprising administering to the subject a therapeutically effective amount of an immunogenic composition according to the present invention.

22 Claims, No Drawings

Specification includes a Sequence Listing.

(56) References Cited

OTHER PUBLICATIONS

GenBank Accession No. JX896321.1, Xiao et al., "Porcine parvovirus 5 isolate IA469 clone 1, complete genome". College of Veterinary Medicine, Iowa State University, Department of Veterinary Diagnostic and Production Animal Medicine, 2013, pp. 1-3.

GenBank Accession No. AFM73871.1 Cadar et al., "Comparative genetic characterization, phylogeography and evolution of novel porcine parvoviruses". Direct Submission, Mar. 31, 2012, Jun. 26, 2012, 1 page.

Martinez, Concepción, et al. "Production of porcine parvovirus empty capsids with high immunogenic activity." Vaccine 10.10 (1992): 684-690.

Mengeling, W. L., K. M. Lager, and A. C. Vorwald. "The effect of porcine parvovirus and porcine reproductive and respiratory syndrome virus on porcine reproductive performance." Animal reproduction science 60 (2000): 199-210.

Puig et al: "Vaccination with the Mixed Administration of ERYSENG® Parvo and UNISTRAIN® PRRS in Gilts Clinically Protects Against a Heterologous PRRSV Infection". European Symposium of Porcine Health Management, Jun. 11, 2015, p. 1.

Streck, André Felipe, et al. "High rate of viral evolution in the capsid protein of porcine parvovirus." Journal of general virology 92.11 (2011): 2628-2636.

Xu, Yigang, and Yijing Li. "Induction of immune responses in mice after intragastric administration of Lactobacillus casei producing porcine parvovirus VP2 protein." Appl. Environ. Microbiol. 73.21 (2007): 7041-7047.

Zeeuw, E. J. L., et al. "Study of the virulence and cross-neutralization capability of recent porcine parvovirus field isolates and vaccine viruses in experimentally infected pregnant gilts." Journal of general virology 88.2 (2007):420-427.

Zhou, Hongchao, Guizhe Yao, and Shangjin Cui. "Production and purification of VP2 protein of porcine parvovirus expressed in an insect-baculovirus cell system." Virology journal 7.1 (2010): 366.

Preuss, T., et al. "Comparison of two different methods for inactivation of viruses in serum." Clin. Diagn. Lab. Immunol. 4.5 (1997): 504-508.

Antonis, Adriaan FG, et al. "A novel recombinant virus-like particle vaccine for prevention of porcine parvovirus-induced reproductive failure." Vaccine 24.26 (2006): 5481-5490.

Cadar, Dániel, et al. "Phylogeny and evolutionary genetics of porcine parvovirus in wild boars." Infection, Genetics and Evolution 12.6 (2012): 1163-1171.

* cited by examiner

VACCINE AGAINST PORCINE PARVOVIRUS

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Porcine parvovirus is an autonomous replicating virus of the Parvovirinae subfamily of the genus *Protoparvovirus* within the family Parvoviridae containing a single stranded DNA molecule of about 5100 nucleotides (Cotmore et al., 2014: Arch Virol.: 159(5): 1239-1247; Molitor et al., 1984: Virology: 137(2):241-54). Only the minus strand of the DNA is packaged into virions. The genome of the virus encodes three capsid proteins (VP1, VP2, VP3) and one non-structural protein (NS1). The capsid of parvovirus is about 22-25 nanometers in diameter and is comprised of VP1 and VP2 subunits. These proteins are derived from alternatively spliced versions of the same RNA molecule and thus overlap in sequence. Further, porcine parvovirus exhibits a high level of sequence similarity to feline pan-leukopenia virus, canine parvoviruses and rodent parvovirus (Ranz et al., 1989: J. gen. Virol: 70:2541-2553).

Although there are differences in porcine parvovirus strains, some being extremely pathogenic and others being less pathogenic or totally non-pathogenic, when the virus becomes established or endemic in a country, the pathogenic strains appear to circulate in the population.

Porcine parvovirus (PPV) infection is a common cause of reproductive failure in breeding pigs throughout the world. Serological studies show that porcine parvovirus is widespread in all swine producing regions of the world with up to 80% of animals showing seroconversion.

The Porcine Parvovirus (PPV) causes reproductive failure in swine, resulting in death and fetal mummification, still births and other reproductive failures in pregnant sows. (Joo & Johnson. 1976. Veterinary Bulletin 46, 653-660; Mengeling. 1978. J. Am. Vet. Med. Assoc. 172, 1291-1294).

The PPV induces reproductive failure when susceptible (non-immune) gilts and sows are infected during pregnancy. This is the only time the virus causes disease. Infection in the pig occurs following ingestion or inhalation of the virus. The PPV then circulates in the bloodstream, and in the pregnant pig crosses the placenta and infects the developing embryos and fetuses. Following natural infection, active immunity develops that probably lasts for the life of the pig. If active immunity occurs before pregnancy then the developing piglets are not affected. At birth the piglets receive maternal immunity in the colostrum from the sow and this maternal immunity lasts for up to 20 weeks of age. The greater the level of active immunity in the sow, the more maternal immunity that she passes onto her piglets. Thereafter, natural infection with PPV may occur.

The disease caused by PPV in pigs is often referred to as a SMEDI (an acronym of stillbirth, mummification, embryonic death, and infertility). If infection occurs at days 0-30 of pregnancy, embryonic mortality may occur resulting in decreased litter size. The most obvious feature following infection at 30-70 days of pregnancy is the birth of mummified piglets. Mummification is the process of sterile digestion of the tissues of the piglets that die in the uterus after the skeleton has started to solidify. PPV infection is also associated with stillbirths and weak born pigs if infection occurs in the later stages of pregnancy. Abortion may also be the result of PPV infection, but is not a common clinical sign of this disease. Overall, PPV infection decreases the number of pigs born per sow per year.

Currently available PPV vaccines are produced by growing native virus on primary cells of porcine origin or in established cell lines. After this, infectious virus is isolated and inactivated with chemical agents to end up with a whole cell killed virus vaccine. However, such processes of growing native infectious virus is problematic for biosecurity and safety considerations. Therefore, there is a need for recombinant PPV vaccines.

Subunit vaccines based on recombinant proteins can suffer from poor immunogenicity owing to incorrect folding of the target protein or poor presentation to the immune system. Further, whole cell killed vaccines present all antigens of the native virus, whereas in a subunit vaccine there is a limitation to a specific amino acid sequence.

Recombinant PPV vaccines have been already described in the prior art, however, until now only whole cell killed vaccines are commercially available. Thus, it seems that so far no appropriate recombinant PPV subunit vaccines have been developed and shown to be effective and safe. The recombinant PPV subunit vaccines described so far have not been tested in controlled, laboratory challenge experiments. The recombinant PPV subunit vaccines that have been evaluated, have not worked as well as whole cell killed PPV vaccines or the recombinant PPV subunit vaccines have not been safe (shown adverse reactions). Therefore, there is still a need for recombinant PPV subunit vaccines being highly effective and safe.

Field isolates of porcine parvovirus (PPV) have been identified that differ genetically and antigenically from the vaccine strains. PPV Genotype 2 virus, PPV-27a, is highly virulent in pregnant gilts after experimental infection, as demonstrated by the high mortality among the fetuses of sows infected with PPV-27a (85%) compared with sows infected with the other strains of PPV, e.g. PPV-NADL-2. However, the currently available commercial vaccines against PPV are based on inactivated whole-virus preparations of PPV genotype 1 strains isolated some 30 years ago (Jozwik et al 2009; Journal of General Virology; 90; 2437-2441). Thus, there is a need for new vaccines protecting against new highly virulent pathogenic strains of PPV that better match PPV in the field.

Further prior art is as follows:

EP 0 551 449 A1 discloses a method for producing a VP2 subunit vaccine against porcine parvovirus.

Cadar D et al. (Infection, Genetics and Evolution 2012, 12: 1163-1171) describe the phylogeny and evolutionary genetics of porcine parvovirus in wild boars.

Streck A F et al. (Journal of General Virology 2011, 92: 2628-2636) describe the high rate of viral evolution in the capsid protein of porcine parvovirus.

WO 88/02026 relates to empty viral capsid vaccines.

Martinez C et al. (Vaccine 1992, 10(10): 684-690), discloses the production of porcine parvovirus empty capsids with high immunogenic activity.

Xu F et al. (Applied and Environmental Microbiology 2007, 73(21): 7041-7047) describe the induction of immune responses in mice after intragastric administration of Lactobacillus casei producing porcine parvovirus VP2 protein.

Moreover, there is a need for new and better vaccines against extremely pathogenic strains of PPV giving a broader protection against different (heterologous) strains (cross-protection) of PPV.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein may be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

The present invention solves the problems inherent in the prior art and provides a distinct advance in the state of the art. Generally, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2.

Advantageously, the experimental data provided by the present invention disclose that the PPV VP2 subunit vaccine of the present invention is safe and efficacious in preventing viremia and PPV infection in fetuses. Further, the experimental data provided by the present invention disclose that the vaccine of the present invention has a broad protection spectrum as the vaccine protects against heterologous North American as well as heterologous European PPV challenge strains.

Advantageously, the experimental data provided by the present invention disclose that the PPV VP2 subunit vaccine of the present invention is as efficacious as the whole killed virus, which is a surprising effect. However, extensive inactivation processes (which are necessary for inactivating native PPV when generating whole killed virus vaccines) could be avoided by utilizing a recombinant subunit vaccine comprised of PPV VP2.

The term "porcine parvovirus" or "PPV" is well known to the person skilled in the art. However, "Porcine parvovirus" is an autonomous replicating virus of the genus parvovirus within the family Parvoviridae containing a single stranded DNA molecule. The genome of the virus encodes three capsid proteins (VP1, VP2, VP3) and one non-structural protein (NS1). The disease caused by PPV in pigs is often referred to as a SMEDI (an acronym of stillbirth, mummification, embryonic death, and infertility). The term "Porcine parvovirus" encompasses all possible strains, genotypes, phenotypes and serotypes of the porcine parvovirus.

The term "viral protein 2" or "VP2" relates to the capsid protein VP2 of the porcine parvovirus. The term "viral protein 2" or "VP2" is well known to the person skilled in the art.

The term "protein", "amino acid" and "polypeptide" are used interchangeably. The term "protein" refers to a sequence of amino acids composed of the natural occurring amino acids as well as derivatives thereof. The naturally occurring amino acids are well known in the art and are described in standard text books of biochemistry. Within the amino acid sequence the amino acid residues are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

The term "wherein the numbering of the amino acid positions refers to the amino acid sequence of wild type PPV VP2" relates to the numbering of amino acid positions referring to the amino acid sequence of full length wild type PPV VP2 protein. Preferably, the numbering of the amino positions as mentioned herein is with reference to a wild type PPV VP2 protein sequence having 579 amino acid residues, including a methionine residue at the (N-terminal) amino acid position 1. The term "wherein the numbering of the amino acid positions refers to the amino acid sequence of wild type PPV VP2" encompasses wild type PPV VP2 as exemplarily given in SEQ ID NO:1 (PPV 27a VP2).

In one aspect of the present invention the PPV VP2 further has at amino acid position 25 an isoleucine residue, and/or at amino acid position 36 a serine residue, and/or at amino acid position 37 an isoleucine residue.

Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein the PPV VP2 further has at amino acid position 25 an isoleucine residue, and/or at amino acid position 36 a serine residue, and/or at amino acid position 37 an isoleucine residue.

In one aspect of the present invention the numbering of the amino acid positions refers to the amino acid sequence as shown in SEQ ID NO:1. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein the numbering of the amino acid positions refers to the amino acid sequence as shown in SEQ ID NO:1.

Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence as shown in SEQ ID NO:1.

In one aspect of the present invention the PPV VP2 is a recombinant PPV VP2.

The term "recombinant" as used herein, in particular refers to a protein molecule which is expressed from a recombinant DNA molecule, such as a polypeptide which is produced by recombinant DNA techniques. An example of such techniques includes the case when DNA encoding the expressed protein (e.g. PPV VP2) is inserted into a suitable expression vector, preferably a baculovirus expression vector, which is in turn used to transfect, or in case of a baculovirus expression vector to infect, a host cell to produce the protein or polypeptide encoded by the DNA. The term "recombinant PPV VP2", as used herein, thus, in particular refers to a protein molecule which is expressed from a recombinant DNA molecule.

In one aspect of the present invention the PPV VP2 is a recombinant baculovirus expressed PPV VP2.

The term "baculovirus" or "baculovirus system" is well known to the person skilled in the art. Further, the term "baculovirus" is specified further below.

In one aspect of the present invention said PPV VP2 comprises or consists of an amino acid sequence having at least 90% sequence identity with the amino acid sequence of SEQ ID NO:1, SEQ ID NO:2 or SEQ ID NO:5 to 16.

In one aspect of the present invention said PPV VP2 comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein said PPV VP2 comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.

In one aspect of the present invention said PPV VP2 comprises or consists of the amino acid sequence of SEQ ID NO:1, or SEQ ID NO:2 or SEQ ID NO:5 to 16 or comprises or consists of any fragment having at least 210, at least 250 or at least 300 contiguous amino acid residues from SEQ ID NO:1, SEQ ID NO:2 or SEQ ID NO:5 to 16. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein said PPV VP2 comprises or consists of the amino acid sequence of SEQ ID NO:1, or SEQ ID NO:2 or SEQ ID NO:5 to 16 or comprises or consists of any fragment having at least 210, at least 250 or at least 300 contiguous amino acid residues from SEQ ID NO:1, SEQ ID NO:2 or SEQ ID NO:5 to 16.

In one aspect of the present invention said PPV VP2 comprises or consists of the amino acid sequence of SEQ ID NO:1, SEQ ID NO:2 or SEQ ID NO:5 to 16. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein said PPV VP2 comprises or consists of the amino acid sequence of SEQ ID NO:1, or SEQ ID NO:2 or SEQ ID NO:5 to 16.

In one aspect of the present invention said PPV VP2 is encoded by a nucleotide sequence encoding an amino acid sequence having at least 90% sequence identity with the amino acid sequence of SEQ ID NO:1, SEQ ID NO:2 or SEQ ID NO:5 to 16.

In one aspect of the present invention said PPV VP2 is encoded by a nucleotide sequence encoding an amino acid sequence at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein said PPV VP2 is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.

In one aspect of the present invention said PPV VP2 is encoded by a nucleotide sequence encoding an amino acid sequence of SEQ ID NO:1, SEQ ID NO:2 or SEQ ID NO:5 to 16. Thus, the present invention provides a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2, and wherein said PPV VP2 is encoded by a nucleotide sequence encoding an amino acid sequence of SEQ ID NO:1, SEQ ID NO:2 or SEQ ID NO:5 to 16.

SEQ ID NO:4 is a codon-optimized PPV 27a VP2 nucleotide sequence which was further modified to have two ClaI restriction enzyme sites (amino acid position 25 is an isoleucine residue, amino acid position 36 is a serine residue, amino acid position 37 is an isoleucine residue) so as to flank the VP2 coding region comprised of Glycine repeats. However, the ClaI restriction enzyme sites were introduced in a manner so as to not disrupt the VP2 coding region. SEQ ID NO:2 is the protein sequence corresponding to SEQ ID NO:4. SEQ ID NO:3 is a codon-optimized PPV 27a VP2 nucleotide sequence (without ClaI restriction enzyme sites). SEQ ID NO:1 is the protein sequence corresponding to SEQ ID NO:3. SEQ ID NO: 5 to 16 disclose further PPV VP2 protein sequences with (SEQ ID NO: 5 to 10) or without (SEQ ID NO: 11 to 16) ClaI restriction enzyme sites.

The terms "nucleic acid" or "nucleic acid sequence" or "nucleotide sequence" or "polynucleotide" are used interchangeably herein and refer to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificial modified one such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5'- or 3'-terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences [i.e., % identity=number of identical positions/total number of positions (i.e. overlapping positions)×100]. Preferably, the two sequences are of the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch [J. Mol. Biol. (48): 444-453 (1970)] algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention may further be used as a "query sequence" to perform a search against public databases to, for example, to identify other family members or related sequences. Such searches may be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the internet homepage of the National Center for Biotechnology Information.

Further, the present invention provides an immunogenic composition comprising the PPV VP2 as described herein. Thus, the present invention provides an immunogenic composition comprising a porcine parvovirus (PPV) viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a PPV infection. The host is also described as "subject". Preferably, any of the hosts or subjects described or mentioned herein are swine.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease will be reduced, the immunogenic composition is described as a "vaccine".

In one aspect of the present invention the immunogenic composition is formulated for a single-dose administration.

The volume for a single-dose has been defined elsewhere herein.

The immunogenic composition is, preferably, administered topically or systemically. Suitable routes of administration conventionally used are oral or parenteral administration, such as intranasal, intravenous, intramuscular, intraperitoneal, subcutaneous, as well as inhalation. However, depending on the nature and mode of action of a compound, the immunogenic composition may be administered by other routes as well. However, most preferred the immunogenic composition is administered intramuscularly.

In one aspect of the present invention the immunogenic composition is administered intramuscularly.

In one aspect of the present invention the immunogenic composition is safe for gilts and/or sows during pregnancy and lactation.

In one aspect of the present invention the immunogenic composition is safe for gilts and/or sows from 30 days of gestation, preferably from 40 days of gestation.

In one aspect of the present invention the immunogenic composition further comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" may include water, saline, dextrose, ethanol, glycerol, and the like. Isotonic agents may include sodium chloride, dextrose, mannitol, sorbitol, and lactose, among others. Stabilizers include albumin and alkali salts of ethylendiamintetracetic acid, among others.

In one aspect of the present invention the pharmaceutically acceptable carrier is a carbomer.

Preferably, the immunogenic composition may further include one or more other immunomodulatory agents such as, e.g. interleukins, interferons, or other cytokines. The amounts and concentrations of adjuvants and additives useful in the context of the present invention may readily be determined by the skilled artisan.

In some aspects, the immunogenic composition of the present invention contains an adjuvant. "Adjuvants" as used herein, may include aluminum hydroxide and aluminum phosphate, saponins e.g., QUIL-A® (commercially available from Brenntag Biosector A/S), QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion may be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the PLURONIC® brand products (commercially available from BASF Corporation), especially L121. See Hunter et al., The Theory and Practical Application of Adjuvants (Ed.Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art may also refer to U.S. Pat. No. 2,909,462 (incorporated by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g., vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant may be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01% to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In one aspect of the present invention the immunogenic composition comprises between about 0.1 µg and 50 µg of the PPV VP2 antigen. Preferably, the immunogenic composition comprises between about 0.2 µg and 40 µg, more preferably between about 0.3 µg and 30 µg, more preferably between about 0.4 µg and 20 µg and even more preferably between about 0.5 µg and 10 µg with an amount of 0.5 µg, 0.75 µg, 1 µg, 1.25 µg, 1.5 µg, 2 µl, 2.5 µg, 3 µg, 3.5 µg, 4 µg, 4.5 µg, 5 µg, 5.5 µg, 6 µg, 6.5 µg, 7 µg, 7.5 µg, 8 µg, 8.5 µg, 9 µg, 9.5 µg or 10 µg of the PPV VP2 antigen most preferred.

In one aspect of the present invention the immunogenic composition is a vaccine.

The term "vaccine" already has been described elsewhere herein. However, in case where the host displays a protective immunological response, such that resistance to new infection will be enhanced and/or the clinical severity of the disease will be reduced, the immunogenic composition is described as a "vaccine".

In one aspect of the present invention the immunogenic composition protects against a homologous and/or a heterologous challenge. Advantageously, the experimental data provided by the present invention disclose that the vaccine of the present invention has a broad protection spectrum as the vaccine protects against heterologous North American as well as heterologous European challenge strains.

The terms "protects" and "prophylaxis" and "preventing" are used interchangeably in this application. These terms have been defined elsewhere.

In one aspect of the present invention the immunogenic composition protects against a challenge with North American and/or European isolates.

The term "North American and European isolates" is well known to the person skilled in the art. The term "North American and/or European isolates" encompasses all isolates which have been or will be isolated in North America and Europe.

In one aspect of the present invention the immunogenic composition is cross protective against North American and/or European isolates.

In one aspect of the present invention the immunogenic composition is effective in the treatment and/or prophylaxis of clinical signs caused by PPV infection in a subject of need. The terms "treatment and/or prophylaxis", "clinical signs" and "of need" have been defined elsewhere.

Further, the present invention provides a polynucleotide comprising a nucleotide sequence which encodes the PPV VP2 as described herein.

Further, the present invention provides a polynucleotide comprising a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence with the nucleotide sequence of SEQ ID NO:3 or SEQ ID NO:4.

Further, the present invention provides a polynucleotide comprising or consisting of the nucleotide sequence of SEQ ID NO:3 or SEQ ID NO:4.

Further, the present invention provides a vector comprising a polynucleotide as described herein.

In one aspect of the present invention the vector is an expression vector.

In one aspect of the present invention the vector is a baculovirus.

The term "vector" is well known to the person skilled in the art. The term "vector" as it is known in the art refers to a polynucleotide construct, typically a plasmid or a virus, used to transmit genetic material to a host cell. Vectors may be, for example, viruses, plasmids, cosmids, or phage. A vector as used herein may be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Vectors and methods for making and/or using vectors (or recombinants) for expression may be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of Escherichia coli B-Galactosidase in Infect Cells with a Baculovirus vector," Molecular and Cellular Biology March 1984, Vol. 4, No. 3, p. 406; EPA0 370 573; U.S. application No. 920,197, filed Oct. 16, 1986; EP patent publication No. 0 265 785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO 93/19183, WO 94/21797, WO 95/11307, WO 95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbachet al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein (all incorporated by reference).

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements. Exemplary regulatory elements in prokaryotes include promoters, operator sequences and a ribosome binding sites. Regulatory elements that are used in eukaryotic cells may include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "promoter" is a nucleotide sequence that permits binding of RNA polymerase and directs the transcription of a gene. Typically, a promoter is located in the 5'-non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter may be inducible, repressible, and/or constitutive. Inducible promoters initiate increased levels of transcription from DNA under their control in response to some change in culture conditions, such as a change in temperature.

As used herein, the term "enhancer" refers to a type of regulatory element that may increase the efficiency of transcription, regardless of the distance or orientation of the enhancer relative to the start site of transcription.

Generation of a viral vector may be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The term "baculovirus" is well known to the person skilled in the art. However, as used herein "baculovirus" in particular means a system for producing a desired protein in an insect cell using a recombinant baculovirus vector designed to express said protein. A baculovirus expression system generally comprises all elements necessary to achieve recombinant protein expression in insect cells, and typically involves the engineering of a baculovirus vector to express a desired protein, the introduction of the engineered baculovirus vector into insect cells, the culturing of the insect cells containing the engineered baculovirus vector in a suitable growth medium such that the desired protein is expressed, and the recovery of the protein. Typically, engineering a baculovirus vector involves the construction and isolation of recombinant baculoviruses in which the coding sequence for a chosen gene is inserted behind the promoter for a nonessential viral gene, wherein most of the presently used baculovirus expression systems are based on the sequence of Autographa californica nuclear polyhedrosis virus (AcMNPV) ((Virology 202 (2), 586-605 (1994), NCBI Accession No.: NC_001623). Baculovirus expression systems are well known in the art and have been described, for example, in "Baculovirus Expression Vectors: A Laboratory Manual" by David R. O'Reilly, Lois Miller, Verne Luckow, pub. by Oxford Univ. Press (1994), "The Baculovirus Expression System: A Laboratory Guide" by Linda A. King, R. D. Possee, published by Chapman & Hall (1992). An exemplary non-limiting example of a baculovirus system for producing a recombinant protein is e.g. described in WO 2006/072065 A2 (incorporated by reference).

Preferred baculovirus vectors include baculovirus such as BACULOGOLD® (BD Biosciences Pharmingen, San Diego, Calif.) or DiamondBac (Sigma Aldrich), in particular provided that the production cells are insect cells. Although the baculovirus expression system is preferred, it is understood by those of skill in the art that other expression systems will work for purposes of the present invention.

Further, the present invention provides a cell comprising the polynucleotide or the vector as described herein. Preferably, the vector is a baculovirus.

The term "cell" is well known to the person skilled in the art. The term "cell" encompasses eukaryotic cell such as an animal cell, protist cell, plant cell, or fungal cell. Preferably the eukaryotic cell is a mammalian cell such as CHO, BHK or COS, or a fungal cell such as *Saccharomyces cerevisiae*, or an insect cell such as Sf9.

In one aspect of the present invention the cell is an insect cell.

"Insect cell" as used herein means a cell or cell culture derived from an insect species. Of particular interest with respect to the present invention are insect cells derived from the species *Spodoptera frugiperda* and *Trichoplusia ni*.

Preferably, the insect cell, as mentioned herein, is a *Spodoptera frugiperda* (Sf) cell or a cell from a cell line derived from *Spodoptera frugiperda*, and is more preferably selected from the group consisting of Sf9 cell and Sf+ cell. Respectively, the insect cells, as mentioned herein, are preferably *Spodoptera frugiperda* (Sf) cells or cells from a cell line derived from *Spodoptera frugiperda*, and are more preferably selected from the group consisting of Sf9 cells and Sf+ cells.

In one aspect of the present invention the insect cell is selected from the group consisting of Sf9 cells and Sf+ cells.

Further, the present invention provides a virus like particle comprising the PPV VP2 as described herein.

The term "virus like particle" (VLP) encompasses a nonreplicating, empty viral shell from a virus. VLPs are generally composed of one or more viral proteins, such as, but not limited to those proteins referred to as capsid, coat, shell, surface and/or envelope proteins, or particle-forming polypeptides derived from these proteins. VLPs may form spontaneously upon recombinant expression of the protein in an appropriate expression system. The presence of VLPs following recombinant expression of viral proteins may be detected using conventional techniques known in the art, such as by electron microscopy, X-ray crystallography, and the like. See, e.g., Baker et al., Biophys. J. (1991) 60:1445-1456; Hagensee et al., J. Virol. (1994) 68:4503-4505. For example, cryoelectron microscopy may be performed on vitrified aqueous samples of the VLP preparation in question, and images recorded under appropriate exposure conditions.

The term "virus like particle" (VLP) also encompasses VLPs which are composed of a plurality of PPV VP2.

In one aspect of the present invention the virus like particle is composed of a plurality of the PPV VP2 as described herein.

Further, the present invention provides a method of producing the PPV VP2 as described herein, comprising transfecting a cell with the vector as described herein.

Further, the present invention provides a method of producing the PPV VP2 as described herein, comprising infecting a cell, preferably an insect cell, with the baculovirus as described herein.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to animals, especially swine. Associated with such container(s) can be a notice in the form prescribed by a governmental agency regulating the manufacture, use or sale of pharmaceuticals or biological products, which notice reflects approval by the agency of manufacture, use or sale for human administration.

Thus, the present invention provides a kit comprising the PPV VP2 or the immunogenic composition as described herein.

In one aspect of the present invention the kit further comprises an instruction letter for the treatment and/or prophylaxis of diseases of swine.

In one aspect of the present invention the kit further comprises an instruction letter for the treatment and/or prophylaxis of PPV infections.

In another aspect of the present invention the PPV virus of the present invention has been inactivated resulting in whole inactivated virus with an viral protein 2 (VP2) as described herein.

Thus, the present invention also refers to an inactivated porcine parvovirus (PPV) having a viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2.

Further, the present invention also refers to an inactivated porcine parvovirus (PPV) having a viral protein 2 (VP2) comprising or consisting of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.

Furthermore, the present invention also refers to an immunogenic composition comprising an inactivated porcine parvovirus (PPV) having a viral protein 2 (VP2) as described herein.

Thus, the present invention also refers to an immunogenic composition comprising an inactivated porcine parvovirus (PPV) having a viral protein 2 (VP2) having at amino acid position 228 a glutamic acid residue or a glutamate residue, and/or at amino acid position 414 a serine residue, and/or at amino acid position 419 a glutamine residue, and/or at amino acid position 436 a threonine residue, wherein the numbering of the amino acid positions refers to the amino acid sequence of wild type PPV VP2.

Thus, the present invention also refers to an immunogenic composition comprising an inactivated porcine parvovirus (PPV) having a viral protein 2 (VP2) comprising or consisting of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.

Any conventional inactivation method may be used for purposes of the present invention. Thus, inactivation may be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, 0-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the PPV. In general, the inaction process is performed until no growth of the PPV can be detected in a suitable cultivation system.

Preferably, the inactivated PPV of the present invention is formalin inactivated, preferably using the concentrations as described hereinabove.

The inactivated PPV of the invention may be incorporated into liposomes using known technology such as that described in Nature, 1974, 252, 252-254 or Journal of Immunology, 1978, 120, 1109-13. In another embodiment of the invention, the inactivated PPV of the invention may be conjugated to suitable biological compounds such as polysaccharides, peptides, proteins, or the like, or a combination thereof.

The present invention also refers to the use of the PPV VP2 as described herein, the immunogenic composition as described herein, the polynucleotide as described herein, the vector as described herein, the cell as described herein, the baculovirus as described herein, and/or the virus like particles as described herein for the preparation of a medicament, preferably of a vaccine.

The present invention also refers to the use of the PPV VP2 as described herein or the immunogenic composition as described herein for the preparation of a medicament for the treatment and/or prevention of an infection with PPV, the reduction, prevention and/or treatment of clinical signs caused by an infection with PPV and/or for the treatment and/or prevention of a disease caused by an infection with PPV.

Further, the present invention provides a method of immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular PPV infection in a herd and/or in the reduction in the severity of clinical signs caused by or associated with the particular PPV infection.

Further, the immunization of a subject in need with the immunogenic compositions as provided herewith, results in preventing infection of a subject by PPV infection. Even more preferably, immunization results in an effective, long-lasting, immunological-response against PPV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a herd are effectively immunized.

Preferably, a herd of subjects is envisaged in this context which normally, i.e. without immunization, would develop clinical signs caused by or associated with a PPV infection. Whether the subjects of a herd are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given herd are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular PPV.

Further, the present invention provides a method of treating and/or preventing clinical signs caused by PPV infection in a subject of need, the method comprising administering to the subject a therapeutically effective amount of an immunogenic composition as described herein.

Advantageously, as shown in the Examples section herein the immunogenic composition as provided herein has been proven to be efficacious in treating and/or preventing clinical signs caused by PPV infection in a subject of need.

The term "treatment and/or prophylaxis" refers to the lessening of the incidence of the particular PPV infection in a herd and/or the reduction in the severity of clinical signs caused by or associated with the particular PPV infection. Thus, the term "treatment and/or prophylaxis" also refers to the reduction of the number of animals in a herd that become infected with the particular PPV (=lessening of the incidence of the particular PPV infection) and/or to the reduction of the severity of clinical signs normally associated with or caused by a PPV infection in a group of animals which animals have received an effective amount of the immunogenic composition as provided herein in comparison to a group of animals which animals have not received such immunogenic composition.

The "treatment and/or prophylaxis" generally involves the administration of an effective amount of the immunogenic composition of the present invention to a subject or herd of subjects in need of or that could benefit from such a treatment/prophylaxis. The term "treatment" refers to the administration of the effective amount of the immunogenic composition once the subject or at least some animals of the herd is/are already infected with such PPV and wherein such animals already show some clinical signs caused by or associated with such PPV infection. The term "prophylaxis" refers to the administration of a subject prior to any infection of such subject with PPV or at least where such animal or none of the animals in a group of animals do not show any clinical signs caused by or associated with the infection by such PPV. The terms "prophylaxis" and "preventing" are used interchangeably in this application.

The term "an effective amount" as used herein means, but is not limited to an amount of antigen, that elicits or is able to elicit an immune response in a subject. Such effective amount is able to lessen the incidence of the particular PPV infection in a herd and/or to reduce the severity of clinical signs of the particular PPV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular PPV.

The term "clinical signs" as used herein refers to signs of infection of a subject from PPV. The clinical signs of infection depend on the pathogen selected. Examples for such clinical signs include but are not limited to transient leukopenia and reproductive failure characterized by embryonic and/or fetal infection and death, or combinations thereof. Examples for clinical signs that are directly observable include reduced litter size, increased mummification of the embryo or fetus per litter, autolysation of the embryo or fetus, reduced size of the embryo or fetus, reduced weight of the embryo or fetus and the alike or combinations thereof. Further examples for such clinical signs include but are not limited to increased viremia, increased viral load within the targeted tissues and blood, increased transmission/shed spread of PPV to penmates and the alike or combinations thereof.

Preferably, the clinical signs lessened in incidence or severity in a treated subject compared to subjects that are either not treated or treated with an immunogenic composition that was available prior to the present invention but subsequently infected by the particular PPV refer to a transient leukopenia and reproductive failure characterized by embryonic and/or fetal infection and death, or combinations thereof.

The term "in need" or "of need", as used herein means that the administration/treatment is associated with the boosting or improvement in health or clinical signs or any other positive medicinal effect on health of the animals (including its embryos or fetuses) which receive the immunogenic composition in accordance with the present invention.

The term "reducing" or "reduced" or "reduction" or "lower" are used interchangeably in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular PPV.

Further, the present invention provides a method of reducing the reproductive failure in a subject, in comparison to a subject of a non-immunized control group of the same species, the method comprising administering to the subject a therapeutically effective amount of an immunogenic composition as described herein.

Advantageously, as shown in the Examples section herein the immunogenic composition as provided herein has been proven to be efficacious in reducing the reproductive failure.

Further, the present invention provides a method of reducing embryonic and fetal death in a subject, in comparison to a subject of a non-immunized control group of the same species, the method comprising administering to the subject a therapeutically effective amount of an immunogenic composition as described herein.

Advantageously, as shown in the Examples section herein the immunogenic composition as provided herein has been proven to be efficacious in reducing embryonic and fetal death.

Furthermore, the present invention provides a method for active immunization of breeding pigs (sows and gilts) for protection of embryos and fetuses against porcine parvovirus infection, the method comprising administering to such pigs (sows and gilts) a therapeutically effective amount of an immunogenic composition as described herein.

In one aspect of the present invention said subject is selected from the group consisting of swine, cattle, cat and dog.

Preferably, said subject is swine. It has to be understood that swine comprises female and male animals. Semen may contain PPV and, for that reason female and male breeding animals are encompassed by the wording "swine". Thus, the wording "swine" comprises male animals such as boars as well as female animals such as gilts and sows.

The term "gilt", as used herein, refers to a porcine, preferably a pig, before and during first gestation/pregnancy. In contrast, the term "sow", as used herein, refers to a porcine, preferably a pig, after first farrowing,—as a positive result of its first gestation/pregnancy.

In one aspect of the present invention said subject is swine, preferably a gilt and/or sow.

In one aspect of the present invention the immunogenic composition is administered once.

It is understood, that a single-dose is administered only once.

The dose volume per subject depends on the route of vaccination and the age of the subject. Preferably, the single-dose has a total volume between about 0.2 ml and 2.5 ml, more preferably between about 0.2 ml and 2.0 ml, even more preferably between about 0.2 ml and 1.75 ml, still more preferably between about 0.2 ml and 1.5 ml, even more preferably between about 0.4 ml and 1.25 ml, even more preferably between about 0.4 ml and 1.0 ml with a single 0.5 ml dose or 1.0 ml dose being the most preferred. Most preferred the single-dose has a total volume of 0.5 ml, 1 ml, 1.5 ml or 2 ml.

In one aspect of the present invention the immunogenic composition is administered at two or more doses.

As shown in the Examples section herein the immunogenic composition as provided herein has been proven to be efficacious after the administration of two doses to a subject of need.

However, the immunogenic composition may be administered at two or more doses, with a first dose being administered prior to the administration of a second (booster) dose. Preferably, the second dose is administered at least 15 days after the first dose. More preferably, the second dose is administered between 15 days and 40 days after the first dose. Even more preferably, the second dose is administered at least 17 days after the first dose. Still more preferably, the second dose is administered between 17 days and 30 days after the first dose. Even more preferably, the second dose is administered at least 19 days after the first dose. Still more preferably, the second dose is administered between 19 days and 25 days after the first dose. Most preferably the second dose is administered at least 21 days after the first dose. Even more preferably, the second dose is administered at about 21 days after the first dose or at 21 days after the first dose. In a preferred aspect of the two-time administration regimen, both the first and second doses of the immunogenic composition are administered in the same amount. Preferably, each dose is in the preferred amounts specified above, with a dose of 1 ml or 2 ml for the first and second dose being most preferred. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

The dose volume per subject depends on the route of vaccination and the age of the subject. Preferably, the total volume is between about 0.2 ml and 5 ml, more preferably between about 0.5 ml and 3.0 ml, even more preferably between about 1.0 ml and 2.5 ml, even more preferably between about 1.0 ml and 2.0 ml. Most preferred the volume is 1 ml, 1.5 ml, 2 ml or 2.5 ml per dose.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, more preferred the immunogenic composition is administered subcutaneously or intramuscularly. Most preferred the immunogenic composition is administered intramuscularly.

In one aspect of the present invention said immunogenic composition is administered intramuscularly.

In one aspect of the present invention said immunogenic composition is administered to gilts and/or sows.

Preferably, the immunogenic composition is administered to gilts and/or sows being at least three 3 months of age, more preferably at least 4 months of age, most preferably at least 5 months of age.

In one aspect of the present invention the immunogenic composition is administered to gilts and/or sows being at least three 3 month of age.

In one aspect of the present invention said immunogenic composition is administered to gilts and/or sows before pregnancy.

In a 2 shot regime, the second dose of said immunogenic composition is preferably administered to gilts and/or sows 2, 3, 4 or 5 weeks before mating/insemination, most preferably about 3 weeks before mating/insemination. Preferably, the first dose of said immunogenic composition is administered to gilts and/or sows 2, 3, 4, 5 or 6 weeks before administering the second dose, most preferably about 3 weeks before administering the second dose. However, after the 2 shot regime has been applied, preferably, gilts and/or sows are revaccinated every 3, 4, 5, 6, 7 or 8 months, most preferably about every 6 months.

In one aspect of the present invention said immunogenic composition is administered to gilts and/or sows during pregnancy and lactation.

In one aspect of the present invention the immunogenic composition is safe for gilts and/or sows during pregnancy and lactation.

In one aspect of the present invention the immunogenic composition is safe for gilts and/or sows from 30 days of gestation, preferably from 40 days of gestation.

Preferably, the immunogenic composition of the present invention comprises between 0.1 µg and 50 µg, preferably between 0.25 µg and 25 µg, more preferably between 0.5 µg and 12.5 µg, even more preferably between 0.5 µg and 5 µg, most preferably between 0.5 µg and 2 µg of the PPV VP2 antigen. More preferably, the immunogenic composition of the present invention comprises the PPV VP2 antigen of the present invention in amounts of about 0.25 µg, 0.5 µg, 0.75 µg, 1 µg, 1.25 µg, 1.5 µg, 1.75 µg, 2 µg, 2.25 µg, 2.5 µg, 2.75 µg, 3 µg, 3.5 µg, 4 µg, 4.5 µg or 5 µg.

In one aspect of the present invention the immunogenic composition comprises between 0.1 µg and 50 µg of the PPV VP2 antigen, preferably between 0.5 µg and 10 µg of the PPV VP2 antigen.

In one aspect of the present invention the immunogenic composition protects against a homologous and/or a heterologous challenge.

In one aspect of the present invention the immunogenic composition protects against a challenge with North American and/or European isolates.

In one aspect of the present invention the immunogenic composition is cross protective against North American and/or European isolates.

In one aspect of the present invention said method results in an improvement in an efficacy parameter selected from the group consisting of: reduced transient leukopenia and reproductive failure characterized by embryonic and/or fetal infection and death, or combinations thereof, in comparison to a subject of a non-immunized control group of the same species.

In one aspect of the present invention said method results in an improvement in an efficacy parameter selected from the group consisting of: reduced litter size, increased mummification of the embryo or fetus per litter, autolysation of the embryo or fetus, reduced size of the embryo or fetus, reduced weight of the embryo or fetus, increased viremia, increased viral load within the targeted tissues and blood, increased transmission/shed spread of PPV to penmates, or combinations thereof, in comparison to a subject of a non-immunized control group of the same species.

Embodiments

The following clauses are also described herein:
1. A porcine parvovirus (PPV) viral protein 2 (VP2) having:
   at amino acid position 228 a glutamic acid residue or a glutamate residue, and/or
   at amino acid position 414 a serine residue, and/or
   at amino acid position 419 a glutamine residue, and/or
   at amino acid position 436 a threonine residue,
   wherein the numbering of the amino acid positions refers to the amino acid sequence of wild type PPV VP2.
2. The PPV VP2 of clause 1, wherein the PPV VP2 further has:
   at amino acid position 25 an isoleucine residue, and/or
   at amino acid position 36 a serine residue, and/or
   at amino acid position 37 an isoleucine residue.
3. The PPV VP2 of clause 1 or 2, wherein the numbering of the amino acid positions refers to the amino acid sequence as shown in SEQ ID NO:1.
4. The PPV VP2 of any one of clauses 1 to 3, wherein the PPV VP2 is a recombinant PPV VP2.
5. The PPV VP2 of any one of clauses 1 to 4, wherein the PPV VP2 is a recombinant baculovirus expressed PPV VP2.
6. The PPV VP2 of any one of clauses 1 to 5, wherein said PPV VP2 comprises or consists of an amino acid sequence having at least 90% sequence identity with the amino acid sequence of SEQ ID NO:1, SEQ ID NO:2 or SEQ ID NO:5 to 16.
7. The PPV VP2 of any one of clauses 1 to 6, wherein said PPV VP2 comprises or consists of an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.
8. The PPV VP2 of any one of clauses 1 to 6, wherein said PPV VP2 comprises or consists of the amino acid sequence of SEQ ID NO:1, or SEQ ID NO:2 or SEQ ID NO:5 to 16 or comprises or consists of any fragment having at least 210, at least 250 or at least 300 contiguous amino acid residues from SEQ ID NO:1, SEQ ID NO:2 or SEQ ID NO:5 to 16.
9. The PPV VP2 of any one of clauses 1 to 6, wherein said PPV VP2 comprises or consists of the amino acid sequence of SEQ ID NO:1, SEQ ID NO:2 or SEQ ID NO:5 to 16.
10. The PPV VP2 of any one of clauses 1 to 9, wherein said PPV VP2 is encoded by a nucleotide sequence encoding an amino acid sequence having at least 90% sequence identity with the amino acid sequence of SEQ ID NO:1, SEQ ID NO:2 or SEQ ID NO:5 to 16.
11. The PPV VP2 of any one of clauses 1 to 10, wherein said PPV VP2 is encoded by a nucleotide sequence encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the amino acid sequence of SEQ ID NO:1, SEQ ID NO:2 or SEQ ID NO:5 to 16.
12. The PPV VP2 of any one of clauses 1 to 11, wherein said PPV VP2 is encoded by a nucleotide sequence encoding an amino acid sequence of SEQ ID NO:1, SEQ ID NO:2 or SEQ ID NO:5 to 16.
13. An immunogenic composition comprising the PPV VP2 of any one of clauses 1 to 12.
14. The immunogenic composition of clause 13, wherein the immunogenic composition is formulated for a single-dose administration.
15. The immunogenic composition of clauses 13 or 14, wherein the immunogenic composition is administered intramuscularly.
16. The immunogenic composition of any one of clauses 13 to 15, wherein the immunogenic composition is safe for gilts and/or sows during pregnancy and lactation.
17. The immunogenic composition of any one of clauses 13 to 16, wherein the immunogenic composition is safe for gilts and/or sows from 30 days of gestation, preferably from 40 days of gestation.
18. The immunogenic composition of any one of clauses 13 to 17, wherein the immunogenic composition further comprises a pharmaceutically acceptable carrier.
19. The immunogenic composition of clause 18, wherein the pharmaceutically acceptable carrier is a carbomer.
20. The immunogenic composition of any one of clauses 13 to 19, wherein the immunogenic composition comprises between 0.1 µg and 50 µg of the PPV VP2 antigen, preferably between 0.5 µg and 10 µg of the PPV VP2 antigen.
21. The immunogenic composition of any one of clauses 13 to 20, wherein the immunogenic composition is a vaccine.
22. The immunogenic composition of any one of clauses 13 to 21, wherein the immunogenic composition protects against a homologous and/or a heterologous challenge.
23. The immunogenic composition of any one of clauses 13 to 22, wherein the immunogenic composition protects against a challenge with North American and/or European isolates.
24. The immunogenic composition of any one of clauses 13 to 23, wherein the immunogenic composition is cross protective against North American and/or European isolates.
25. The immunogenic composition of any one of clauses 13 to 24, wherein the immunogenic composition is effective in the treatment and/or prophylaxis of clinical signs caused by PPV infection in a subject of need.
26. A polynucleotide comprising a sequence which encodes the PPV VP2 of any one of clauses 1 to 12.

27. A polynucleotide comprising a nucleotide sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity with the nucleotide sequence of SEQ ID NO:3 or SEQ ID NO:4.

28. A polynucleotide comprising or consisting of the nucleotide sequence of SEQ ID NO:3 or SEQ ID NO:4.

29. A vector comprising the polynucleotide of any one of clauses 26 to 28.

30. The vector of clause 29, wherein the vector is an expression vector.

31. The vector of clause 29 or 30, wherein the vector is a baculovirus.

32. A cell comprising the polynucleotide of any one of clauses 26 to 28 or the vector of any one of clauses 29 to 31.

33. The cell according to clause 32, wherein the cell is an insect cell.

34. The insect cell according to clause 33, wherein the insect cell is selected from the group consisting of Sf9 cells and Sf+ cells.

35. A virus like particle comprising the PPV VP2 of any one of clauses 1 to 12.

36. The virus like particle of clause 35, wherein the virus like particle is composed of a plurality of the PPV VP2 of any one of clauses 1 to 12.

37. A method of producing the PPV VP2 of any one of clauses 1 to 12, comprising transfecting a cell with the vector of any one of clauses 29 to 31.

38. A method of producing the PPV VP2 of any one of clauses 1 to 12, comprising infecting a cell, preferably an insect cell, with the baculovirus of clause 31.

39. A kit comprising the PPV VP2 or the immunogenic composition of any one of clauses 1 to 25.

40. The kit according to clause 39, wherein the kit further comprises an instruction letter for the treatment and/or prophylaxis of diseases of swine.

41. The kit according to clause 39, wherein the kit further comprises an instruction letter for the treatment and/or prophylaxis of PPV infection.

42. Use of:

the PPV VP2 of any one of clauses 1 to 12, the immunogenic composition of any one of clauses 13 to 25, the polynucleotide of any one of clauses 26 to 28, the vector of any one of clauses 29 to 31, the cell of any one of clauses 32 to 34, the baculovirus of clause 31, and/or the virus like particles of clause 35 or 36 for the preparation of a medicament, preferably of a vaccine.

43. Use of the PPV VP2 of any one of clauses 1 to 12 or the immunogenic composition of any one of clauses 13 to 25 for the preparation of a medicament for the treatment and/or prevention of an infection with PPV, the reduction, prevention and/or treatment of clinical signs caused by an infection with PPV and/or for the treatment and/or prevention of a disease caused by an infection with PPV.

44. A method of immunizing a subject comprising administering to such subject an immunogenic composition of any one of clauses 13 to 25.

45. A method of treating and/or preventing clinical signs caused by PPV infection in a subject of need, the method comprising administering to the subject a therapeutically effective amount of an immunogenic composition according to any one of clauses 13 to 25.

46. A method of reducing the reproductive failure in a subject, in comparison to a subject of a non-immunized control group of the same species, the method comprising administering to the subject a therapeutically effective amount of an immunogenic composition according to any one of clauses 13 to 25.

47. A method of reducing embryonic and fetal death in a subject, in comparison to a subject of a non-immunized control group of the same species, the method comprising administering to the subject a therapeutically effective amount of an immunogenic composition according to any one of clauses 13 to 25.

48. The method of any one of clauses 44 to 47, wherein said subject is selected from the list consisting of swine, cattle, cat and dog.

49. The method of any one of clauses 44 to 48, wherein said subject is swine, preferably a gilt and/or sow.

50. The method of any one of clauses 44 to 49, wherein the immunogenic composition is administered once.

51. The method of any one of clauses 44 to 49, wherein the immunogenic composition is administered at two or more doses.

52. The method of any one of clauses 44 to 51, wherein the immunogenic composition is administered intramuscularly.

53. The method of any one of clauses 44 to 52, wherein the immunogenic composition is administered to gilts and/or sows.

54. The method of any one of clauses 44 to 53, wherein the immunogenic composition is administered to gilts and/or sows being at least three 3 month of age.

55. The method of any one of clauses 44 to 54, wherein the immunogenic composition is administered to gilts and/or sows before pregnancy.

56. The method of any one of clauses 44 to 54, wherein the immunogenic composition is administered to gilts and/or sows during pregnancy and lactation.

57. The method of any one of clauses 44 to 56, wherein the immunogenic composition is safe for gilts and/or sows during pregnancy and lactation.

58. The method of any one of clauses 44 to 57, wherein the immunogenic composition is safe for gilts and/or sows from 30 days of gestation, preferably from 40 days of gestation.

59. The method of any one of clauses 44 to 58, wherein the immunogenic composition comprises between 0.1 μg and 50 μg of the PPV VP2 antigen, preferably between 0.5 μg and 10 μg of the PPV VP2 antigen.

60. The method of any one of clauses 44 to 59, wherein the immunogenic composition protects against a homologous and/or a heterologous challenge.

61. The method of any one of clauses 44 to 60, wherein the immunogenic composition protects against a challenge with North American and/or European isolates.

62. The method of any one of clauses 44 to 61, wherein the immunogenic composition is cross protective against North American and/or European isolates.

63. The method of any one of clauses 44 to 62, wherein said method results in an improvement in an efficacy parameter selected from the group consisting of: reduced transient leukopenia and reproductive failure characterized by embryonic and/or fetal infection and death, or combinations thereof, in comparison to a subject of a non-immunized control group of the same species.

64. The immunogenic composition for use of any one of clauses 44 to 63, wherein said method results in an improvement in an efficacy parameter selected from the group consisting of: reduced litter size, increased mummification of the embryo or fetus per litter, autolysation of the embryo or fetus, reduced size of the embryo or fetus, reduced weight of the embryo or fetus, increased viremia, increased viral load within the targeted tissues and blood, increased transmission/shed spread of PPV to penmates, or combinations thereof, in comparison to a subject of a non-immunized control group of the same species.

65. The immunogenic composition of any one of clauses 13 to 25 for use in a method of immunizing a subject comprising administering said immunogenic composition to such subject.

66. The immunogenic composition of any one of clauses 13 to 25 for use in a method of treating or preventing clinical signs caused by PPV infection in a subject of need, the method comprising administering to the subject a therapeutically effective amount of said immunogenic composition.

67. The immunogenic composition of any one of clauses 13 to 25 for use in a method of reducing the reproductive failure in a subject, in comparison to a subject of a non-immunized control group of the same species, the method comprising administering to the subject a therapeutically effective amount of said immunogenic composition.

68. The immunogenic composition of any one of clauses 13 to 25 for use in a method of reducing embryonic and fetal death in a subject, in comparison to a subject of a non-immunized control group of the same species, the method comprising administering to the subject a therapeutically effective amount of said immunogenic composition.

69. The immunogenic composition for use of any one of clauses 65 to 68, wherein said subject is selected from the list consisting of swine, cattle, cat and dog.

70. The immunogenic composition for use of any one of clauses 65 to 69, wherein said subject is swine, preferably a gilt and/or sow.

71. The immunogenic composition for use of any one of clauses 65 to 70, wherein the immunogenic composition is administered once.

72. The immunogenic composition for use of any one of clauses 65 to 70, wherein the immunogenic composition is administered at two or more doses.

73. The immunogenic composition for use of any one of clauses 65 to 72, wherein the immunogenic composition is administered intramuscularly.

74. The immunogenic composition for use of any one of clauses 65 to 73, wherein the immunogenic composition is administered to gilts and/or sows.

75. The immunogenic composition for use of any one of clauses 65 to 74, wherein the immunogenic composition is administered to gilts and/or sows being at least three 3 month of age.

76. The immunogenic composition for use of any one of clauses 65 to 75, wherein the immunogenic composition is administered to gilts and/or sows before pregnancy.

77. The immunogenic composition for use of any one of clauses 65 to 75, wherein the immunogenic composition is administered to gilts and/or sows during pregnancy and lactation.

78. The immunogenic composition for use of any one of clauses 65 to 77, wherein the immunogenic composition is safe for gilts and/or sows during pregnancy and lactation.

79. The immunogenic composition for use of any one of clauses 65 to 78, wherein the immunogenic composition is safe for gilts and/or sows from 30 days of gestation, preferably from 40 days of gestation.

80. The immunogenic composition for use of any one of clauses 65 to 78, wherein the immunogenic composition comprises between 0.1 µg and 50 µg of the PPV VP2 antigen, preferably between 0.5 µg and 10 µg of the PPV VP2 antigen.

81. The immunogenic composition for use of any one of clauses 65 to 80, wherein the immunogenic composition protects against a homologous and/or a heterologous challenge.

82. The immunogenic composition for use of any one of clauses 65 to 81, wherein the immunogenic composition protects against a challenge with North American and/or European isolates.

83. The immunogenic composition for use of any one of clauses 65 to 82, wherein the immunogenic composition is cross protective against North American and/or European isolates.

84. The immunogenic composition for use of any one of clauses 65 to 83, wherein said method results in an improvement in an efficacy parameter selected from the group consisting of: reduced transient leukopenia and reproductive failure characterized by embryonic and/or fetal infection and death, or combinations thereof, in comparison to a subject of a non-immunized control group of the same species.

85. The immunogenic composition for use of any one of clauses 65 to 84, wherein said method results in an improvement in an efficacy parameter selected from the group consisting of: reduced litter size, increased mummification of the embryo or fetus per litter, autolysation of the embryo or fetus, reduced size of the embryo or fetus, reduced weight of the embryo or fetus, increased viremia, increased viral load within the targeted tissues and blood, increased transmission/shed spread of PPV to penmates, or combinations thereof, in comparison to a subject of a non-immunized control group of the same species.

86. A method for active immunization of breeding pigs (sows and gilts) for protection of embryos and fetuses against porcine parvovirus infection, the method comprising administering to such pigs (sows and gilts) a therapeutically effective amount of an immunogenic composition of clauses 13 to 25.

87. The immunogenic composition of any one of clauses 13 to 25 for use in a method for active immunization of breeding pigs (sows and gilts) for protection of embryos and fetuses against porcine parvovirus infection, the method comprising administering to such pigs (sows and gilts) a therapeutically effective amount of said immunogenic composition.

EXAMPLES

The following examples are set forth below to illustrate specific embodiments of the present invention. These examples are merely illustrative and are understood not to limit the scope or the underlying principles of the present invention.

Example 1

Preparation of Subunit PPV Vaccine

The PPV VP2 antigen was selected to be expressed in baculovirus-infected insect cells based on the German PPV 27a isolate. Porcine parvovirus (PPV) 27a VP2 nucleotide sequence is obtained from Genbank Accession AY684871.1.

The PPV 27a VP2 coding region is reverse-translated and codon-optimized for Drosophila (SEQ ID NO:4 and SEQ ID NO:3). The codon-optimized PPV 27a VP2 gene was chemically synthesized at Integrated DNA Technologies. The PPV 27a gene was then subcloned into the baculovirus transfer vector pVL1393, and co-transfected with the linearized baculovirus DiamondBac backbone into Sf9 insect cells to generate recombinant baculovirus containing the PPV 27a VP2 gene under control of the polyhedrin promoter.

When expressed in Sf9 insect cells the PPV VP2 self-assembled into a non-enveloped VLP.

The PPV VP2 antigen was adjuvanted with a carbomer (e.g., CARBOPOL®).

Example 2

Proof of Concept Study of the PPV Vaccine

In all animal studies, the animals are in good health and nutritional status before the study is initiated. Prior to the randomization procedure a health examination is conducted. Non-medicated feed is used through the duration of the study. Feed rations are appropriate for the age, condition, and species of test animal according to facility standard operating procedure. Water is provided ad libitum throughout the study.

The objective of this vaccination-challenge study is to establish proof of concept dose determination efficacy for a pre-breeding subunit Porcine Parvovirus (PPV) vaccine (see Example 1). Gilts are vaccinated and bred prior to challenge with a live virulent PPV isolate (PPV 002346-5; a North American Strain) at approximately 40 days of gestation (dG). Fetuses are evaluated for PPV infection at approximately 90 dG.

The study design is described in Table 1.

Post-vaccination, the gilts are synchronized (via administration of MATRIX®; altrenogest, Intervet Schering-Plough Animal Health; per label for 14 consecutive days, D18 to D31) and then bred between D35 and D42. Fifty-four of the 67 gilts became pregnant. On D80 (approximately 40 dG), NTX gilts are necropsied, and the remaining gilts were inoculated with 6 mL of PPV strain PPV002346-5 (a North American Strain) at 4.25 $\log_{10}TCID_{50}$ per dose (2 mL intramuscularly and 2 mL per nostril intranasally). Gilts were bled weekly except during synchronization and breeding (D35-D70). Serology was performed on sera from D0, D7, D14, D21, D28 and D73; serology and polymerase chain reaction (PCR) (as described in Jozwik et al. 2009; Journal of General Virology, 90, 2437-2441) for viremia was performed on sera from D80, D87, D94, D101, D108, D115, D122, and D128. Gilts were necropsied on D129 or D130 (approximately 90 dG). At necropsy, each reproductive tract was removed, and the position of the fetus in the uterus, the fetal condition, size and weight were recorded. Samples of thoracic wash and lung from each fetus were collected. Thoracic wash samples were collected aseptically from each fetus. Briefly, 3 ml of sterile PBS were injected into the thoracic cavity with a sterile needle and syringe. Fluid was aspirated back into the syringe and injected into an appropriate, sterile SST (serum separator tube) of suitable size. Thoracic washes were tested for the presence of PPV by PCR and for the presence of PPV antibody by hemagglutination inhibition (HI). Lung tissue was stored frozen.

Gilt Viremia (PPV)

All gilts were negative for PPV viremia prior to challenge on D0, D73 (data not shown) and D80 (Table 2). All

TABLE 1

Study Design

| Treatment | | Vaccination | Insemination | Pregnancy Evaluation | Challenge | Necropsy |
|---|---|---|---|---|---|---|
| T1 | Negative Control | 2 mL on D0 right neck IM & 2 mL on D21 left neck IM | D34-D42 | D71 | 6 mL on D80 (~40 dG) PPV 002346-5 right neck IM and IN | D129/130 (~90 dG) |
| T2 | PPV 10 µg | | | | | |
| T3 | Positive Control (whole cell inactivated PPV) | | | | | |
| NTX | None | Not applicable | | | Not applicable | D79 (39 dG) |

NTX = Non-Treated/Non-Challenged Control;
IN = intranasal;
IM = intramuscular;
dG = days of gestation.

Sixty-seven gilts originated from a herd that previously tested negative for PPV with no prior history of reproductive disease or vaccination against PPV were used. Gilts were randomized into 6 treatment groups (T) of n=9 commingled into 3 pens receiving vaccination on D0 and boostered on D21: T1 NC (negative control of water for injection), T2 PPV 10 µg, T3 PC (positive control; whole, inactivated porcine parvovirus (PPV), *Erysipelothrix rhusiopathiae*, *Leptospira canicola*, *L. grippotyphosa*, *L. hardjo*, *L. icterohaemorrhagiae*, and *L. Pomona*; commercially available; used according to manufacturer's manual). Three non-treated control (NTX) gilts are included, one per pen.

negative controls are viremic on D87, and 4/7 are viremic on D94.

Post-vaccination T3 gilts seroconvert following booster vaccination. T2 had a serological response to initial vaccination and stays seropositive after the booster vaccination. T1 control gilts remained serologically negative for PPV until challenge. Post-challenge, all negative control gilts were viremic on D87 (seven days after challenge). One T3 gilt was viremic on D87. All other gilts are not viremic at these time points (see Table 2).

NTX gilts remained seronegative and their fetuses were all PPV negative by PCR on thoracic wash samples.

TABLE 2

Frequency distribution of PPV-positive (PCR) gilts when challenged with PPV at 40 days of gestation (dG) on D80.

| | | Day of Study (dG = days of gestation) | | | | | | | |
|---|---|---|---|---|---|---|---|---|---|
| | Treatment/Description | D80 dG 40 | D87 dG 47 | D94 dG 54 | D101 dG 61 | D108 dG 68 | D115 dG 75 | D122 dG 82 | D128 dG 89 |
| T1 | Negative Control | 0/7 | 7/7 | 4/7 | 0/7 | 0/7 | 0/7 | 0/7 | 0/7 |
| T2 | 10 µg PPV | 0/8 | 0/8 | 0/8 | 0/8 | 0/8 | 0/8 | 0/8 | 0/8 |
| T3 | Positive Control (whole cell inactivated PPV) | 0/9 | 1/9 | 0/9 | 0/9 | 0/9 | 0/8 | 0/8 | 0/8 |
| NTX | None | 0/3 | NA | NA | NA | NA | NA | NA | NA |

NA = not applicable.

Fetus Results

All of the NTX fetuses were considered normal on D80 necropsy (Table 3). At final necropsy on D129 and D130, 22.5% of T1 (Negative Control) fetuses were normal while 98.39% of fetuses in T3 and 97.62% of fetuses in T2 were normal. The average size and weight of T1 (Negative Control) fetuses was 11.5 cm and 168.8 g, respectively, while the average size and weight of fetuses in T2 was 17.5 cm and 590.1 g, respectively.

All T4 (NTX) fetuses were PPV negative determined by PCR on thoracic wash samples (see Table 3). PPV infection was confirmed in 67/80 T1 Negative Control fetuses (83.75%). Sixty-two of the 67 Negative Control fetuses confirmed to be PPV infected were mummies. In contrast, PPV infection was confirmed only in 0.79% in T2 fetuses.

Based on the conclusion parameter for establishing efficacy as stated in the European Pharmacopoeia (monograph 01/2008:0965), all vaccines [including the Positive Control (whole cell inactivated PPV)] meet criteria for protection from infection (>80% fetuses negative for PPV).

TABLE 3

Litter details: number, size, weight and condition of fetuses and laboratory confirmation of PPV infection (PCR on thoracic wash samples).

| | | Treatment | | |
|---|---|---|---|---|
| Description | T1 NC | T2 PPV 10 µg | T3 Positive Control (whole cell inactivated PPV) | T4 NTX* |
| # of gilts | 5 | 8 | 9 | 3 |
| Total # fetuses | 80 | 126 | 124 | 44 |
| Avg. litter size | 16.0 | 15.8 | 13.8 | 14.7 |
| Fetal Condition: | | | | |
| Mummies | 62 | 3 | 2 | 0 |
| Normal | 18 | 123 | 122 | 44 |
| % Normal | 22.50 | 97.62 | 98.39 | 100.0 |
| Average size (cm) | 11.5 | 17.5 | 17.8 | 6.0 |
| Average weight (g) | 168.8 | 590.1 | 580.3 | 11.9 |
| Laboratory Confirmation of PPV Infection: | | | | |
| # PPV+ fetuses | 67 | 1 | 3 | 0 |
| % positive | 83.75 | 0.79 | 2.42 | 0.0 |
| % protected | 16.25 | 99.21 | 97.58 | |

*NTX fetuses necropsied at 50 days of gestation

NC = Negative Control

Conclusion

The PPV vaccine of the present invention showed protection of fetuses after virulent heterologous PPV challenge. The study results show that the vaccine was safe when administered pre-breeding and efficacious in significantly reducing viremia, and transplacental infection in fetuses. Further, it has been shown that the vaccine protects against a heterologous North American PPV challenge strain. Furthermore, it has been shown that the subunit PPV VP2 protein is as efficacious as the whole killed virus.

Example 3

Establishing the Minimum Immunizing Dose of the PPV Vaccine-Protection Against Heterologous North American PPV Strain The objective of this vaccination-challenge study is to establish the minimum immunizing dose (MID) for the Porcine Parvovirus (PPV) vaccine. Gilts are challenged with a live virulent PPV serotype 1 isolate (PPV 002346-5) at approximately 40 days of gestation (dG). A vaccine is considered efficacious if ≥80% of fetuses in the vaccinated group are negative for PPV after challenge. Supportive parameters include fetus size, weight and condition, gilt viremia status post-challenge and gilt serological status.

Gilts (with no prior history of reproductive disease or vaccination against PPV) were randomized into treatment groups: T01 negative control (Product matched placebo (PMP)) and T02=1.0 µg PPV/2 mL dose). Non-treated/non-challenged (NTX) gilts were randomly assigned to pens as controls for general health status.

Gilts were given 2 mL of the appropriate treatment intramuscularly on D0 and D21. Post-vaccination, gilts were bred between D37 and D50, and then evaluated for pregnancy status on D74. On D81, gestating gilts were challenged with 6.77 $\log_{10}$TCID50/6 mL of PPV serotype 1 intramuscularly and intranasally. Gilts were bled weekly except during estrus synchronization and breeding (D36-D73). Hemagglutination Inhibition (HI) assays were performed on sera from D7, D14, D21, D28 and D35; HI and polymerase chain reaction (PCR) (see Example 2) for viremia were performed on sera from D-3, D74, D80, D88, D95, D102 and D127. Gilts were necropsied on D128 and D129 (approximately 90 dG). At necropsy, the reproductive tract of each sow was removed, and the position of each fetus in the uterus, the fetal condition, size and weight were recorded. Thoracic wash samples (see Example 2) were collected from each fetus and tested for the presence of PPV by PCR.

Gilt Viremia (PPV)

The vaccines were considered safe since animals showed no abnormal body temperature 24 hours or 48 hours post-vaccination, no abnormal local reactions attributable to the vaccine and no clinical signs related to vaccination (data not shown).

All gilts were negative for PPV viremia prior to vaccination, prior to challenge on D74, and on D80. Thus, post-vaccination, no clinical signs related to vaccine administration are observed. On D88, all ten T01 gilts were viremic, and all vaccinated gilts were negative. All other blood samples on D95, D102 and D127 were negative for PPV viremia for all treatment groups (Table 4).

TABLE 4

Frequency distribution of PPV-positive (PCR) gilts when challenged with PPV at ~40 days of gestation (dG) on D81.

| | | Day of Study/Days of Gestation (dG) | | | | | |
|---|---|---|---|---|---|---|---|
| | Treatment/Description | D74 dG 32 | D80 dG 38 | D88 dG 46 | D95 dG 53 | D102 dG 60 | D127 dG 85 |
| T01 | Negative Control | 0/12 | 0/12 | 10/10* | 0/10 | 0/10 | 0/10 |
| T02 | PPV (1.0 µg/dose) | 0/12 | 0/12 | 0/12 | 0/12 | 0/12 | 0/12 |

*2 gilts have been diagnosed as not pregnant and have, therefore, been removed from the group

Fetus Results

At final necropsy on D128 and D129, 38% of T01 (Negative Control) fetuses were normal condition while 95% of fetuses in the vaccine group were normal condition. The average size and weight of T01 (Negative Control) fetuses was 14.4 cm and 245.9 g, respectively, while the average size and weight of fetuses from the vaccinated dams was 19.3 cm and 550 g, respectively (Table 5). Thus, the vaccine group met the criteria for protection from infection with PPV as the conclusion parameter for PPV efficacy established by the Ph. Eur. 01/2008:0965 is >80% fetuses in a treatment group must be negative for PPV.

PPV infection was confirmed in 113/146 of Negative Control (T01) fetuses (77%). However, PPV infection in the vaccinated group (T02) was only 10%.

TABLE 5

Litter details: number, size, weight and condition of fetuses and laboratory confirmation of PPV infection (PCR on thoracic wash samples).

| | Treatment | |
|---|---|---|
| Description | T01 Negative Control | T02 PPV 1 µg |
| # of gilts | 10 | 11 |
| Total # fetuses | 146 | 148 |
| Avg. litter size | 14.6 | 13.5 |
| Fetal Condition: | | |
| # Necrotic (%) | 9 (6%) | 0 (0%) |
| # Mummies (%) | 82 (56%) | 8 (5%) |
| # Normal (%) | 55 (38%) | 140 (95%) |
| Average size (cm) | 14.4 | 19.3 |
| Average weight (g) | 245.9 | 550.0 |
| Laboratory Confirmation of PPV Infection: | | |
| # Thoracic wash positive fetuses (%) | 113 (77%) | 15 (10%) |
| % protected | | 90% |

# = number, % = percent

Conclusion

The PPV VP2 subunit vaccine of the present invention showed protection of fetuses after challenge with a virulent heterologous PPV. The study results reveal that the vaccine is safe and efficacious in preventing viremia in gilts and PPV infection in fetuses when using only 1 µg of PPV VP2 subunit vaccine. Further, it is shown that the vaccine protects against a heterologous North American challenge strain.

Example 4

Establishing the Minimum Immunizing Dose of the PPV Vaccine-Protection Against Heterologous EU PPV Strain The objective of this study is to evaluate the onset of immunity of the Porcine Parvovirus Vaccine (also called PPV or PPV VP2 vaccine herein). In addition, safety and efficacy is evaluated using a randomized, blinded, negative controlled vaccination-challenge study design.

Gilts were randomly assigned to three groups. In groups 1 and 2 gilts were vaccinated twice, with a three week interval (on D0 and D21). The second dose was given three weeks before mating. All treatments were administered by the intramuscular (IM) route in a 2 mL volume. Group 2 received the PPV vaccine, whereas group 1 was the placebo group which received a sterile diluent as control product and group 3 served as strict control, without any treatment.

The gilts are oestrus synchronized and three weeks after the second vaccination they were artificially inseminated. Animals that got pregnant were challenged on D84 between the 39th and 42nd day of gestation with a virulent, heterologous PPV strain.

On D132-135, at about the 90th day of gestation, the gilts were euthanized, necropsied and the fetuses were evaluated.

Evaluation of PPV Viremia in Gilts Pre- and Post-Challenge by PCR

All animals were negative for PPV by PCR at D-6 and D-1 before vaccination fulfilling the inclusion criteria. Post vaccination all animals in the strict control and control product group were negative for PPV antigen until challenge, therefore, a PPV infection before challenge can be excluded.

Viremia was investigated at 7 (D90), 14 (D97) and 21 (D104) days post challenge and at the day of necropsy. After challenge no viremia was detected in the vaccinated animals, viremia occurred only in the non-vaccinated control animals.

On D90, (7 days post challenge) already 95% of the non-vaccinated control animals were positive for PPV. On D97 still 60% of these animals had a positive result while on D104 all animals were tested negative for PPV. In contrast, in the vaccinated group all animals tested on day D90, D97 or D104 were negative for PPV.

TABLE 6

| Study Design | | | | |
|---|---|---|---|---|
| Group | 1st Treatment D0 (2 mL right side of neck IM) | 2nd Treatment D21 (2 mL left side of neck IM) | Challenge D84 6.0 $Log_{10}TCID_{50}/6$ mL) dose (~40 dG) 2 mL right neck IM and 2 mL per nostril intranasal | Necropsy |
| 1 (Negative Control) | Control Product | Control Product | PPV EU Strain 401/09 (198669) | D132 to D135 |
| 2 | PPV (1 µg/dose) | PPV (1 µg/dose) | PPV EU Strain 401/09 (198669) | D132 to D135 |
| 3 (Strict Control) | — | — | No Challenge | D83 |

TABLE 7

Number of animals with viremia after challenge

| | 7 days post challenge (D90) | 14 days post challenge (D97) | 21 days post challenge (D104) |
|---|---|---|---|
| Control | 19/20 (95%) | 12/20 (60%) | 0/20 |
| PPV | 0/20 | 0/20 | 0/20 |

Fetus Results

The percentage of PPV infected fetus was of 91.4% in the Control group, but only 4.3% in the PPV group (see Table 8).

TABLE 8

Percentage of positive fetuses per group and litter size

| Group | N gilts | N fetuses | N positive fetuses | % PPV positive (PCR) fetuses per treatment[1] | N Average litter size | Min % postive fetuses | Max % positive fetuses per litter |
|---|---|---|---|---|---|---|---|
| Control | 19 | 269 | 246 | 91.4 | 14.2 | 57 | 100 |
| PPV | 19 | 231 | 10 | 4.3 | 12.2 | 0 | 20 |

[1]Number of positive PPV fetuses/Number of fetuses per group.

N Total number

Evaluation of Condition of Fetuses

All fetuses were evaluated for their condition and allocated to three categories: normal, mummified and autolyzed.

The majority of mummified and autolyzed fetuses were found in the control group. Only 39.8% of fetuses in this group were of normal condition while in the vaccinated groups 97.4% (PPV group) of fetuses had a normal condition (see Table 9).

TABLE 9

Fetal condition

| Group | [% normal] | [% autolyzed] | [% mummified] | [N (total)] |
|---|---|---|---|---|
| Control | 39.8% | 12.3% | 48.0% | 269 |
| PPV | 97.4% | 0.9% | 1.7% | 231 |

Conclusion

The PPV vaccine of the present invention shows protection of fetuses after virulent heterologous PPV challenge indicating that the vaccine is safe and efficacious in preventing viremia and PPV infection in fetuses when using only 1 μg of vaccine. Further, it has been shown that the vaccine also protects against a heterologous European challenge strain of PPV. Thus, the vaccine has a broad protection spectrum as the vaccine protects against heterologous North American as well as heterologous European challenge strains.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A porcine parvovirus (PPV) subunit vaccine comprising:
   an effective amount of a PPV viral protein 2 (VP2) antigen comprising an isoleucine residue at amino acid position 25, a serine residue at amino acid position 36, an isoleucine residue at amino acid position 37, a glutamic acid residue or a glutamate residue at amino acid position 228, a serine residue at amino acid position 414, a glutamine residue at amino acid position 419, and a threonine residue at amino acid position 436,
   wherein amino acid position numbering refers to an amino acid sequence of wild type PPV VP2.

2. The PPV subunit vaccine of claim 1, wherein the amino acid sequence of wild type PPV VP2 has 579 amino acid residues.

3. The PPV subunit vaccine of claim 1, wherein the PPV VP2 antigen comprises an amino acid sequence having at least 90% sequence identity to at least one of SEQ ID NOs: 2, 5, 6, 7, 8, 9, or 10.

4. The PPV subunit vaccine of claim 1, further comprising an adjuvant.

5. The PPV subunit vaccine of claim 1, further comprising a pharmaceutically acceptable carrier.

6. The PPV subunit vaccine of claim 5, wherein the pharmaceutically acceptable carrier is a carbomer.

7. The PPV subunit vaccine of claim 1, wherein the PPV subunit vaccine has between 0.1 µg and 50 µg of the PPV VP2 antigen.

8. The PPV subunit vaccine of claim 1, wherein the PPV subunit vaccine has between 0.5 µg and 10 µg of the PPV VP2 antigen.

9. A method of vaccinating an animal, comprising:
   administering to the animal a PPV subunit vaccine comprising an effective amount of a PPV VP2 antigen,
   wherein the PPV VP2 antigen comprises an isoleucine residue at amino acid position 25, a serine residue at amino acid position 36, an isoleucine residue at amino acid position 37, a glutamic acid residue or a glutamate residue at amino acid position 228, a serine residue at amino acid position 414, a glutamine residue at amino acid position 419, and a threonine residue at amino acid position 436, and
   wherein amino acid position numbering refers to an amino acid sequence of wild type PPV VP2.

10. The method of claim 9, wherein the amino acid sequence of wild type PPV VP2 has 579 amino acid residues.

11. The method of claim 9, wherein the PPV VP2 antigen comprises an amino acid sequence having at least 90% sequence identity to at least one of SEQ ID NOs: 2, 5, 6, 7, 8, 9, or 10.

12. The method of claim 9, wherein the PPV subunit vaccine further comprises an adjuvant.

13. The method of claim 9, wherein the PPV subunit vaccine further comprises a pharmaceutically acceptable carrier.

14. The method of claim 13, wherein the pharmaceutically acceptable carrier is a carbomer.

15. The method of claim 9, wherein the PPV subunit vaccine has between 0.1 µg and 50 µg of the PPV VP2 antigen.

16. The method of claim 9, wherein the PPV subunit vaccine has between 0.5 µg and 10 µg of the PPV VP2 antigen.

17. The method of claim 9, wherein the animal is a swine.

18. The method of claim 17, wherein the swine is a gilt or sow.

19. The method of claim 9, wherein a protective immune response effective to reduce or eliminate subsequent PPV-infection clinical signs in the animal, relative to a non-vaccinated control animal of the same species, is elicited by administration of the PPV subunit vaccine.

20. The method of claim 9, wherein a protective immune response effective to reduce reproductive failure risk in the animal, relative to a non-vaccinated control animal of the same species, is elicited by administration of the PPV subunit vaccine.

21. The method of claim 9, wherein a protective immune response effective to reduce embryonic and fetal death risk in the animal, relative to a non-vaccinated control animal of the same species, is elicited by administration of the PPV subunit vaccine.

22. The method of claim 9, wherein the animal is a breeding pig, and wherein a protective immune response effective to reduce PPV infection in an embryo and/or a fetus of the breeding pig, relative to a non-vaccinated control breeding pig of the same species, is elicited by administration of the PPV subunit vaccine.

* * * * *

SEQUENCE LISTING

```
<160> NUMBER OF SEQ ID NOS: 16

<210> SEQ ID NO 1
<211> LENGTH: 579
<212> TYPE: PRT
<213> ORGANISM: Porcine parvovirus

<400> SEQUENCE: 1

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
            20                  25                  30

Gly Arg Gly Ala Gly Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
```

```
            195                 200                 205
Arg Tyr Tyr Leu Ser Cys Thr Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 2
<211> LENGTH: 579
<212> TYPE: PRT
<213> ORGANISM: Porcine parvovirus
```

<400> SEQUENCE: 2

```
Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415
```

```
Asn Leu Gln Asn Thr Asn Asn Gly Thr Leu Leu Pro Ser Asp Pro Ile
            420                 425                 430
Gly Gly Lys Thr Asn Met His Phe Met Asn Thr Leu Asn Thr Tyr Gly
        435                 440                 445
Pro Leu Thr Ala Leu Asn Asn Thr Ala Pro Val Phe Pro Asn Gly Gln
    450                 455                 460
Ile Trp Asp Lys Glu Leu Asp Thr Asp Leu Lys Pro Arg Leu His Val
465                 470                 475                 480
Thr Ala Pro Phe Val Cys Lys Asn Asn Pro Pro Gly Gln Leu Phe Val
                485                 490                 495
Lys Ile Ala Pro Asn Leu Thr Asp Phe Asn Ala Asp Ser Pro Gln
            500                 505                 510
Gln Pro Arg Ile Ile Thr Tyr Ser Asn Phe Trp Trp Lys Gly Thr Leu
        515                 520                 525
Thr Phe Thr Ala Lys Met Arg Ser Ser Asn Met Trp Asn Pro Ile Gln
    530                 535                 540
Gln His Thr Thr Thr Ala Glu Asn Ile Gly Asn Tyr Ile Pro Thr Asn
545                 550                 555                 560
Ile Gly Gly Ile Lys Met Phe Pro Glu Tyr Ser Gln Leu Ile Pro Arg
                565                 570                 575
Lys Leu Tyr

<210> SEQ ID NO 3
<211> LENGTH: 1760
<212> TYPE: DNA
<213> ORGANISM: Porcine parvovirus

<400> SEQUENCE: 3
ggatccgcca ccatgtccga gaacgtggag cagcacaacc cgataaacgc aggcacagag      60
ctgtcggcga ctggcaatga gagcggaggc ggaggcggcg gaggaggtgg acgcggcgca     120
ggcggagtgg gcgtttcgac cggaagcttc aataatcaaa ccgagtttca gtacctgggc     180
gagggtttgg tgcggattac ggctcacgcg tcccgactga tacatctcaa tatgccggag     240
catgagacct acaagcgtat ccatgtcctg aactcggaat cgggcgtcgc cggtcagatg     300
gtccaagatg atgctcatac tcagatggtg acaccctgga gcttgataga tgccaacgca     360
tggggcgtgt ggttcaaccc tcgcgattgg cagctgataa gcaataacat gacagaaatc     420
aatttggtta gtttcgagca agagatattt aatgtcgtgc tgaaaaccat cacagagagc     480
gccacgagcc ccccgacgaa gatttacaat aacgacctga cggcgtcctt gatggtcgcc     540
ttggacacaa taacaccct cccgtacacc ccgcggcccc ccgcagcga ccctgggc     600
ttttatccct ggctgccac caagccaacg cagtatcgct actacctgag ttgtacacga     660
aatttgaatc cgccgacata cactggtcag tcggagcaga tcacggacag cattcaaacg     720
ggcctgcact ccgatatcat gttttacacg atagagaacg cagtacccat ccacctgctg     780
cgtacgggag atgagttctc gaccggtatc tatcattttg acacaaaacc cttgaaattg     840
acgcacagtt ggcaaaccaa tcgctcgctg gccttgcccc caaagttgtt gacggaaccc     900
accaccgagg gtgaccaaca cccaggcact ctccccgcag caaatacccg caagggctat     960
catcaaacga tcaacaatag ctataccgag gctaccgcca ttcggccagc acaggtggga    1020
tacaacacac cttacatgaa ctttgaatac tccaacggcg gccgttcct gaccccgata    1080
gttccgaccg ccgacactca gtacaacgat gacgagccga acggcgccat caggtttacc    1140
```

```
atgggctatc agcacggtca attgacaact tcgtcgcaag aactggaacg ctatacattc    1200
aaccctcaga gtaagtgtgg ccgggcaccc aaacaacagt tcaaccagca atccccactg    1260
aacctgcaga ataccaacaa tggcacgctg ctgccatccg atcccattgg aggaaagacc    1320
aacatgcatt tcatgaacac gctgaataca tacggaccac tgaccgccct gaacaatacc    1380 gcaccegtct tccctaatgg ccagatctgg gataaagagc tggatacgga cctgaagccc    1440
cgactccacg tgactgcgcc ctttgtgtgc aaaaataacc caccgggaca gttgttcgtc    1500
aaaatagccc ccaacttgac cgacgacttc aatgcagaca gccctcagca gccgcgaatc    1560
atcacctatt cgaacttctg gtggaagggc acgctgactt tcacggctaa gatgcgctcg    1620
agcaatatgt ggaacccaat ccagcaacat accacaaccg ctgaaaatat tggcaattac    1680
atccctacga atataggcgg aataaagatg tttccggagt attcccagct cattccacgc    1740
aagctgtatt aagcggccgc                                                1760

<210> SEQ ID NO 4
<211> LENGTH: 1760
<212> TYPE: DNA
<213> ORGANISM: Porcine parvovirus

<400> SEQUENCE: 4
ggatccgcca ccatgtccga gaacgtggag cagcacaacc cgataaacgc aggcacagag      60
ctgtcggcga ctggcaatga atcgatcggc ggaggcggcg gaggaggtgg acgcggatcg     120
atcggagtgg gcgtttcgac cggaagcttc aataatcaaa ccgagtttca gtacctgggc     180 gagggttttgg tgcggattac ggctcacgcg tcccgactga tacatctcaa tatgccggag    240
catgagacct acaagcgtat ccatgtcctg aactcggaat cgggcgtcgc cggtcagatg     300
gtccaagatg atgctcatac tcagatggtg acaccctgga gcttgataga tgccaacgca    360
tggggcgtgt ggttcaaccc tgcggattgg cagctgataa gcaataacat gacagaaatc     420
aatttggtta gtttcgagca agagatattt aatgtcgtgc tgaaaaccat cacagagagc     480
gccacgagcc ccccgacgaa gatttacaat aacgacctga cggcgtcctt gatggtcgcc     540
ttggacacaa ataacaccct cccgtacacc cccgcggccc ccgcagcga ccctgggc      600 ttttatccct ggctgcccac caagccaacg cagtatcgct actacctgag ttgtacacga    660
aatttgaatc cgccgacata cactggtcag tcggagcaga tcacggacag cattcaaacg    720
ggcctgcact ccgatatcat gttttacacg atagagaacg cagtacccat ccacctgctg    780
cgtacgggag atgagttctc gaccggtatc tatcattttg acacaaaacc cttgaaattg    840
acgcacagtt ggcaaaccaa tcgctcgctg ggcttgcccc caagttgtt gacggaaccc     900 accaccgagg gtgaccaaca cccaggcact ctcccccgcag caaatacccg caagggctat    960
catcaaacga tcaacaatag ctataccgag gctaccgcca ttcggccagc acaggtggga   1020
tacaacacac cttacatgaa ctttgaatac tccaacggcg gccgttcct gaccccgata   1080 gttccgaccg ccgacactca gtacaacgat gacgagccga acggcgccat caggtttacc   1140
atgggctatc agcacggtca attgacaact tcgtcgcaag aactggaacg ctatacattc    1200
aaccctcaga gtaagtgtgg ccgggcaccc aaacaacagt tcaaccagca atccccactg    1260
aacctgcaga ataccaacaa tggcacgctg ctgccatccg atcccattgg aggaaagacc    1320
aacatgcatt tcatgaacac gctgaataca tacggaccac tgaccgccct gaacaatacc    1380 gcaccegtct tccctaatgg ccagatctgg gataaagagc tggatacgga cctgaagccc    1440
cgactccacg tgactgcgcc ctttgtgtgc aaaaataacc caccgggaca gttgttcgtc    1500
```

-continued

```
aaaatagccc ccaacttgac cgacgacttc aatgcagaca gccctcagca gccgcgaatc  1560
atcacctatt cgaacttctg gtggaagggc acgctgactt tcacggctaa gatgcgctcg  1620
agcaatatgt ggaacccaat ccagcaacat accacaaccg ctgaaaatat tggcaattac  1680
atccctacga ataggcgg aataaagatg tttccggagt attcccagct cattccacgc  1740
aagctgtatt aagcggccgc                                              1760

<210> SEQ ID NO 5
<211> LENGTH: 579
<212> TYPE: PRT
<213> ORGANISM: Porcine parvovirus

<400> SEQUENCE: 5
```

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Thr
305                 310                 315                 320

```
Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Asp Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Arg Met Phe Pro Glu Tyr Ser Gln Leu Ile Pro Arg
                565                 570                 575

Lys Leu Tyr

<210> SEQ ID NO 6
<211> LENGTH: 579
<212> TYPE: PRT
<213> ORGANISM: Porcine parvovirus

<400> SEQUENCE: 6

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110
```

```
Asp Ala Asn Ala Trp Gly Val Trp Phe Asn Pro Ala Asp Trp Gln Leu
            115                 120                 125
Ile Ser Asn Asn Met Thr Glu Ile Asn Leu Val Ser Phe Glu Gln Glu
130                 135                 140
Ile Phe Asn Val Val Leu Lys Thr Ile Thr Glu Ser Ala Thr Ser Pro
145                 150                 155                 160
Pro Thr Lys Ile Tyr Asn Asn Asp Leu Thr Ala Ser Leu Met Val Ala
                165                 170                 175
Leu Asp Thr Asn Asn Thr Leu Pro Tyr Thr Pro Ala Ala Pro Arg Ser
            180                 185                 190
Glu Thr Leu Gly Phe Tyr Pro Trp Leu Pro Thr Lys Pro Thr Gln Tyr
        195                 200                 205
Arg Tyr Tyr Leu Ser Cys Thr Arg Asn Leu Asn Pro Pro Thr Tyr Thr
    210                 215                 220
Gly Gln Ser Glu Gln Ile Thr Asp Ser Ile Gln Thr Gly Leu His Ser
225                 230                 235                 240
Asp Ile Met Phe Tyr Thr Ile Glu Asn Ala Val Pro Ile His Leu Leu
                245                 250                 255
Arg Thr Gly Asp Glu Phe Ser Thr Gly Ile Tyr His Phe Asp Thr Lys
            260                 265                 270
Pro Leu Lys Leu Thr His Ser Trp Gln Thr Asn Arg Ser Leu Gly Leu
        275                 280                 285
Pro Pro Lys Leu Leu Thr Glu Pro Thr Thr Glu Gly Asp Gln His Pro
    290                 295                 300
Gly Thr Leu Pro Ala Ala Asn Thr Arg Lys Gly Tyr His Gln Thr Ile
305                 310                 315                 320
Asn Asn Ser Tyr Thr Glu Ala Thr Ala Ile Arg Pro Ala Gln Val Gly
                325                 330                 335
Tyr Asn Thr Pro Tyr Met Asn Phe Glu Tyr Ser Asn Gly Gly Pro Phe
            340                 345                 350
Leu Thr Pro Ile Val Pro Thr Ala Asp Thr Gln Tyr Asn Asp Asp Glu
        355                 360                 365
Pro Asn Gly Ala Ile Arg Phe Thr Met Gly Tyr Gln His Gly Gln Leu
    370                 375                 380
Thr Thr Ser Ser Gln Glu Leu Glu Arg Tyr Thr Phe Asn Pro Gln Ser
385                 390                 395                 400
Lys Cys Gly Arg Ala Pro Lys Gln Gln Phe Asn Gln Ser Pro Leu
                405                 410                 415
Asn Leu Gln Asn Thr Asn Asn Gly Thr Leu Leu Pro Ser Asp Pro Ile
            420                 425                 430
Gly Gly Lys Thr Asn Met His Phe Met Asn Thr Leu Asn Thr Tyr Gly
        435                 440                 445
Pro Leu Thr Ala Leu Asn Asn Thr Ala Pro Val Phe Pro Asn Gly Gln
    450                 455                 460
Ile Trp Asp Lys Glu Leu Asp Thr Asp Leu Lys Pro Arg Leu His Val
465                 470                 475                 480
Thr Ala Pro Phe Val Cys Lys Asn Asn Pro Pro Gly Gln Leu Phe Val
                485                 490                 495
Lys Ile Ala Pro Asn Leu Thr Asp Asp Phe Asn Ala Asp Ser Pro Gln
            500                 505                 510
Gln Pro Arg Ile Ile Thr Tyr Ser Asn Phe Trp Trp Lys Gly Thr Leu
        515                 520                 525
Thr Phe Thr Ala Lys Met Arg Ser Ser Asn Met Trp Asn Pro Ile Gln
```

```
                    530                 535                 540
Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 7
<211> LENGTH: 579
<212> TYPE: PRT
<213> ORGANISM: Porcine parvovirus

<400> SEQUENCE: 7

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
                20                  25                  30

Gly Arg Gly Ser Ile Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
        50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
```

-continued

```
                325                 330                 335
Tyr Asn Thr Pro Tyr Met Asn Phe Glu Tyr Ser Asn Gly Gly Pro Phe
            340                 345                 350
Phe Ile Pro Ile Val Pro Thr Ala Asp Thr Gln Tyr Asn Asp Asp Glu
        355                 360                 365
Pro Asn Gly Gly Ile Arg Phe Thr Met Gly Tyr Gln His Gly Gln Leu
    370                 375                 380
Ile Thr Ser Ser Gln Glu Val Glu Arg Tyr Thr Phe Asn Pro Gln Arg
385                 390                 395                 400
Lys Cys Gly Arg Gly Ala Lys Gln Gln Phe Asn Gln Gln Ser Pro Leu
                405                 410                 415
Asn Ile Gln Asn Thr Asn Asn Gly Thr Ile Leu Pro Ser Asp Pro Ile
            420                 425                 430
Gly Gly Lys Thr Asn Met His Phe Met Asn Thr Pro Asn Thr Tyr Gly
        435                 440                 445
Pro Leu Thr Ala Val Asn Asn Thr Ala Pro Val Phe Pro Asn Gly Gln
    450                 455                 460
Ile Trp Asp Lys Glu Leu Asp Thr Asp Leu Lys Pro Arg Leu His Val
465                 470                 475                 480
Thr Ala Pro Phe Val Cys Lys Asn Asn Pro Pro Gly Gln Leu Phe Val
                485                 490                 495
Lys Ile Ala Pro Asn Leu Thr Asp Asp Phe Asn Ala Asp Ser Pro Gln
            500                 505                 510
Gln Pro Arg Ile Ile Thr Tyr Ser Asn Phe Trp Trp Lys Gly Thr Leu
        515                 520                 525
Thr Phe Thr Ala Lys Met Arg Ser Ser Asn Met Trp Asn Pro Ile Gln
    530                 535                 540
Gln His Thr Thr Thr Ala Glu Asn Ile Gly Asn Tyr Ile Pro Thr Asn
545                 550                 555                 560
Ile Gly Gly Ile Lys Met Phe Pro Glu Tyr Ser Gln Leu Ile Pro Arg
                565                 570                 575
Lys Leu Tyr
```

<210> SEQ ID NO 8
<211> LENGTH: 579
<212> TYPE: PRT
<213> ORGANISM: Porcine parvovirus

<400> SEQUENCE: 8

```
Met Ser Glu Asn Val Glu Gln His Asn Pro Ile Asn Ala Gly Thr Glu
1               5                   10                  15
Leu Ser Ala Thr Gly Asn Glu Ser Ile Gly Gly Gly Gly Gly Gly Gly
            20                  25                  30
Gly Arg Gly Ser Ile Gly Val Gly Val Ser Thr Gly Ser Phe Asn Asn
        35                  40                  45
Gln Thr Glu Phe Gln Tyr Leu Gly Glu Gly Leu Val Arg Ile Thr Ala
    50                  55                  60
His Ala Ser Arg Leu Ile His Leu Asn Met Pro Glu His Glu Thr Tyr
65                  70                  75                  80
Lys Arg Ile His Val Leu Asn Ser Glu Ser Gly Val Ala Gly Gln Met
                85                  90                  95
Val Gln Asp Asp Ala His Thr Gln Met Val Thr Pro Trp Ser Leu Ile
            100                 105                 110
Asp Ala Asn Ala Trp Gly Val Trp Phe Asn Pro Ala Asp Trp Gln Leu
```

```
            115                 120                 125
Ile Ser Asn Asn Met Thr Glu Ile Asn Leu Val Ser Phe Glu Gln Ala
    130                 135                 140
Ile Phe Asn Val Val Leu Lys Thr Ile Thr Glu Ser Ala Thr Ser Pro
145                 150                 155                 160
Pro Thr Lys Ile Tyr Asn Asn Asp Leu Thr Ala Ser Leu Met Val Ala
                165                 170                 175
Leu His Thr Asn Asn Thr Leu Pro Tyr Thr Pro Ala Ala Pro Arg Ser
                180                 185                 190
Glu Thr Leu Gly Phe Tyr Pro Trp Leu Pro Thr Lys Pro Thr Gln Tyr
                195                 200                 205
Arg Tyr Tyr Leu Ser Cys Ile Arg Asn Leu Asn Pro Pro Thr Tyr Thr
                210                 215                 220
Gly Gln Ser Glu Gln Ile Thr Asp Ser Ile Gln Thr Gly Leu His Ser
225                 230                 235                 240
Asp Ile Met Phe Tyr Thr Ile Glu Asn Ala Val Pro Ile His Leu Leu
                245                 250                 255
Arg Thr Gly Asp Glu Phe Ser Thr Gly Ile Tyr His Phe Asp Thr Lys
                260                 265                 270
Pro Leu Lys Leu Thr His Ser Trp Gln Thr Asn Arg Ser Leu Gly Leu
                275                 280                 285
Pro Pro Lys Leu Leu Thr Glu Pro Thr Thr Glu Gly Asp Gln His Pro
290                 295                 300
Gly Thr Leu Pro Ala Ala Asn Thr Arg Lys Gly Tyr His Gln Thr Ile
305                 310                 315                 320
Asn Asn Ser Tyr Thr Glu Ala Thr Ala Ile Arg Pro Ala Gln Val Gly
                325                 330                 335
Tyr Asn Thr Pro Tyr Met Asn Phe Glu Tyr Ser Asn Gly Gly Pro Phe
                340                 345                 350
Leu Thr Pro Ile Val Pro Thr Ala Asp Thr Gln Tyr Asn Asp Asp Glu
                355                 360                 365
Pro Asn Gly Ala Ile Arg Phe Thr Met Asp Tyr Gln His Gly His Leu
                370                 375                 380
Thr Thr Ser Ser Gln Glu Leu Glu Arg Tyr Thr Phe Asn Pro Gln Ser
385                 390                 395                 400
Lys Cys Gly Arg Thr Pro Lys Gln Gln Phe Asn Gln Gln Ser Pro Leu
                405                 410                 415
Asn Leu Gln Asn Thr Asn Asn Gly Thr Leu Leu Pro Ser Asp Pro Ile
                420                 425                 430
Gly Gly Lys Thr Asn Met His Phe Met Asn Thr Leu Asn Thr Tyr Gly
                435                 440                 445
Pro Leu Thr Ala Leu Asn Asn Thr Ala Pro Val Phe Pro Asn Gly Gln
                450                 455                 460
Ile Trp Asp Lys Glu Leu Asp Thr Asp Leu Lys Pro Arg Leu His Val
465                 470                 475                 480
Thr Ala Pro Phe Val Cys Lys Asn Asn Pro Pro Gly Gln Leu Phe Val
                485                 490                 495
Lys Ile Ala Pro Asn Leu Thr Asp Asp Phe Asn Ala Asp Ser Pro Gln
                500                 505                 510
Gln Pro Arg Ile Ile Thr Tyr Ser Asn Phe Trp Trp Lys Gly Thr Leu
                515                 520                 525
Thr Phe Thr Ala Lys Met Arg Ser Ser Asn Met Trp Asn Pro Ile Gln
                530                 535                 540
```

-continued

```
Gln His Thr Thr Thr Ala Glu Asn Ile Gly Lys Tyr Ile Pro Thr Asn
545                 550                 555                 560

Ile Gly Gly Ile Lys Met Phe Pro Glu Tyr Ser Gln Leu Ile Pro Arg
            565                 570                 575

Lys Leu Tyr

<210> SEQ ID NO 9
<211> LENGTH: 579
<212> TYPE: PRT
<213> ORGANISM: Porcine parvovirus

<400> SEQUENCE: 9

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
                20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335
```

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Ser Thr Leu Asn Thr Tyr Gly
                435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 10
<211> LENGTH: 579
<212> TYPE: PRT
<213> ORGANISM: Porcine parvovirus

<400> SEQUENCE: 10

Met Ser Glu Asn Val Glu Gln His Asn Pro Ile Asn Ala Gly Thr Glu
1               5                   10                  15

Leu Ser Ala Thr Gly Asn Glu Ser Ile Gly Gly Gly Gly Gly Gly Gly
            20                  25                  30

Gly Arg Gly Ser Ile Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

```
Ile Ser Asn Asn Met Thr Glu Ile Asn Leu Val Ser Phe Glu Gln Glu
            130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
        210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
        370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
        450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
530                 535                 540
```

```
Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
            565                 570                 575

Lys Leu Tyr
```

<210> SEQ ID NO 11
<211> LENGTH: 579
<212> TYPE: PRT
<213> ORGANISM: Porcine parvovirus

<400> SEQUENCE: 11

```
Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
                20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
        50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Ile Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Glu Gly Asp Gln His Pro
290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335
```

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
            355                 360                 365

Pro Asn Gly Ala Ile Arg Phe Thr Met Asp Tyr Gln His Gly Gln Leu
            370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
            405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
            435                 440                 445

Pro Leu Thr Ala Leu Asn Asn Thr Ala Pro Val Phe Pro Asn Gly Gln
            450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
            485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
            515                 520                 525

Thr Phe Thr Ala Lys Met Arg Ser Ser Asn Met Trp Asn Pro Ile Gln
            530                 535                 540

Gln His Thr Thr Thr Ala Glu Asn Ile Gly Asn Tyr Ile Pro Thr Asn
545                 550                 555                 560

Ile Gly Gly Ile Arg Met Phe Pro Glu Tyr Ser Gln Leu Ile Pro Arg
            565                 570                 575

Lys Leu Tyr

<210> SEQ ID NO 12
<211> LENGTH: 579
<212> TYPE: PRT
<213> ORGANISM: Porcine parvovirus

<400> SEQUENCE: 12

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly
            20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
            50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
            85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
            115                 120                 125

```
Ile Ser Asn Asn Met Thr Glu Ile Asn Leu Val Ser Phe Glu Gln Glu
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
    290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
            340                 345                 350

Leu Thr Pro Ile Val Pro Thr Ala Asp Thr Gln Tyr Asn Asp Asp Glu
        355                 360                 365

Pro Asn Gly Ala Ile Arg Phe Thr Met Gly Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Asn Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
```

```
            545                 550                 555                 560
Ile Gly Gly Ile Lys Met Phe Pro Glu Tyr Ser Gln Leu Ile Pro Arg
                    565                 570                 575

Lys Leu Tyr

<210> SEQ ID NO 13
<211> LENGTH: 579
<212> TYPE: PRT
<213> ORGANISM: Porcine parvovirus

<400> SEQUENCE: 13

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
                20                  25                  30

Gly Arg Gly Ala Gly Gly Val Gly Val Ser Thr Gly Ser Phe Asn Asn
            35                  40                  45

Gln Thr Glu Phe Gln Tyr Leu Gly Glu Gly Leu Val Arg Ile Thr Ala
        50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
130                 135                 140

Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
            260                 265                 270

Pro Leu Lys Leu Thr His Ser Trp Gln Thr Asn Arg Ser Leu Gly Leu
        275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
```

```
            340                 345                 350

Phe Ile Pro Ile Val Pro Thr Ala Asp Thr Gln Tyr Asn Asp Asp Glu
            355                 360                 365

Pro Asn Gly Gly Ile Arg Phe Thr Met Gly Tyr Gln His Gly Gln Leu
    370                 375                 380

Ile Thr Ser Ser Gln Glu Val Glu Arg Tyr Thr Phe Asn Pro Gln Arg
385                 390                 395                 400

Lys Cys Gly Arg Gly Ala Lys Gln Gln Phe Asn Gln Gln Ser Pro Leu
                405                 410                 415

Asn Ile Gln Asn Thr Asn Asn Gly Thr Ile Leu Pro Ser Asp Pro Ile
            420                 425                 430

Gly Gly Lys Thr Asn Met His Phe Met Asn Thr Pro Asn Thr Tyr Gly
        435                 440                 445

Pro Leu Thr Ala Val Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 14
<211> LENGTH: 579
<212> TYPE: PRT
<213> ORGANISM: Porcine parvovirus

<400> SEQUENCE: 14

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
            20                  25                  30

Gly Arg Gly Ala Gly Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Ala
```

```
            130                 135                 140
Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu His Thr Asn Asn Thr Leu Pro Tyr Thr Pro Ala Ala Pro Arg Ser
                180                 185                 190

Glu Thr Leu Gly Phe Tyr Pro Trp Leu Pro Thr Lys Pro Thr Gln Tyr
            195                 200                 205

Arg Tyr Tyr Leu Ser Cys Ile Arg Asn Leu Asn Pro Pro Thr Tyr Thr
        210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
                260                 265                 270

Pro Leu Lys Leu Thr His Ser Trp Gln Thr Asn Arg Ser Leu Gly Leu
            275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Ile
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
            355                 360                 365

Pro Asn Gly Ala Ile Arg Phe Thr Met Asp Tyr Gln His Gly His Leu
        370                 375                 380

Thr Thr Ser Ser Gln Glu Leu Glu Arg Tyr Thr Phe Asn Pro Gln Ser
385                 390                 395                 400

Lys Cys Gly Arg Thr Pro Lys Gln Gln Phe Asn Gln Ser Pro Leu
                405                 410                 415

Asn Leu Gln Asn Thr Asn Asn Gly Thr Leu Leu Pro Ser Asp Pro Ile
                420                 425                 430

Gly Gly Lys Thr Asn Met His Phe Met Asn Thr Leu Asn Thr Tyr Gly
            435                 440                 445

Pro Leu Thr Ala Leu Asn Asn Thr Ala Pro Val Phe Pro Asn Gly Gln
        450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
530                 535                 540

Gln His Thr Thr Thr Ala Glu Asn Ile Gly Lys Tyr Ile Pro Thr Asn
545                 550                 555                 560
```

Ile Gly Gly Ile Lys Met Phe Pro Glu Tyr Ser Gln Leu Ile Pro Arg
            565                 570                 575

Lys Leu Tyr

<210

Leu Thr Pro Ile Val Pro Thr Ala Asp Thr Gln Tyr Asn Asp Asp Glu
            355                 360                 365

Pro Asn Gly Ala Ile Arg Phe Thr Met Gly Tyr Gln His Gly Gln Leu
    370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
            420                 425                 430

Gly Gly Lys Thr Asn Met His Phe Met Ser Thr Leu Asn Thr Tyr Gly
        435                 440                 445

Pro Leu Thr Ala Leu Asn Asn Thr Ala Pro Val Phe Pro Asn Gly Gln
    450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
            500                 505                 510

Gln Pro Arg Ile Ile Thr Tyr Ser Asn Phe Trp Trp Lys Gly Thr Leu
        515                 520                 525

Thr Phe Thr Ala Lys Met Arg Ser Ser Asn Met Trp Asn Pro Ile Gln
    530                 535                 540

Gln His Thr Thr Thr Ala Glu Asn Ile Gly Asn Tyr Ile Pro Thr Asn
545                 550                 555                 560

Ile Gly Gly Ile Lys Met Phe Pro Glu Tyr Ser Gln Leu Ile Pro Arg
                565                 570                 575

Lys Leu Tyr

<210> SEQ ID NO 16
<211> LENGTH: 579
<212> TYPE: PRT
<213> ORGANISM: Porcine parvovirus

<400> SEQUENCE: 16

Met Ser Glu Asn Val Glu Gln His Asn Pro Ile Asn Ala Gly Thr Glu
1               5                   10                  15

Leu Ser Ala Thr Gly Asn Glu Ser Gly Gly Gly Gly Gly Gly Gly Gly
            20                  25                  30

Gly Arg Gly Ala Gly Gly Val Gly Val Ser Thr Gly Ser Phe Asn Asn
        35                  40                  45

Gln Thr Glu Phe Gln Tyr Leu Gly Glu Gly Leu Val Arg Ile Thr Ala
    50                  55                  60

His Ala Ser Arg Leu Ile His Leu Asn Met Pro Glu His Glu Thr Tyr
65                  70                  75                  80

Lys Arg Ile His Val Leu Asn Ser Glu Ser Gly Val Ala Gly Gln Met
                85                  90                  95

Val Gln Asp Asp Ala His Thr Gln Met Val Thr Pro Trp Ser Leu Ile
            100                 105                 110

Asp Ala Asn Ala Trp Gly Val Trp Phe Asn Pro Ala Asp Trp Gln Leu
        115                 120                 125

Ile Ser Asn Asn Met Thr Glu Ile Asn Leu Val Ser Phe Glu Gln Glu
    130                 135                 140

```
Ile Phe Asn Val Val Leu Lys Thr Ile Thr Glu Ser Ala Thr Ser Pro
145                 150                 155                 160

Pro Thr Lys Ile Tyr Asn Asn Asp Leu Thr Ala Ser Leu Met Val Ala
                165                 170                 175

Leu Asp Thr Asn Asn Thr Leu Pro Tyr Thr Pro Ala Ala Pro Arg Ser
            180                 185                 190

Glu Thr Leu Gly Phe Tyr Pro Trp Leu Pro Thr Lys Pro Thr Gln Tyr
        195                 200                 205

Arg Tyr Tyr Leu Ser Cys Thr Arg Asn Leu Asn Pro Pro Thr Tyr Thr
    210                 215                 220

Gly Gln Ser Glu Gln Ile Thr Asp Ser Ile Gln Thr Gly Leu His Ser
225                 230                 235                 240

Asp Ile Met Phe Tyr Thr Ile Glu Asn Ala Val Pro Ile His Leu Leu
                245                 250                 255

Arg Thr Gly Asp Glu Phe Ser Thr Gly Ile Tyr His Phe Asp Thr Lys
                260                 265                 270

Pro Leu Lys Leu Thr His Ser Trp Gln Thr Asn Arg Ser Leu Gly Leu
                275                 280                 285

Pro Pro Lys Leu Leu Thr Glu Pro Thr Thr Glu Gly Asp Gln His Pro
290                 295                 300

Gly Thr Leu Pro Ala Ala Asn Thr Arg Lys Gly Tyr His Gln Thr Thr
305                 310                 315                 320

Asn Asn Ser Tyr Thr Glu Ala Thr Ala Ile Arg Pro Ala Gln Val Gly
                325                 330                 335

Tyr Asn Thr Pro Tyr Met Asn Phe Glu Tyr Ser Asn Gly Gly Pro Phe
                340                 345                 350

Leu Thr Pro Ile Val Pro Thr Ala Asp Thr Gln Tyr Asn Asp Asp Glu
                355                 360                 365

Pro Asn Gly Ala Ile Arg Phe Thr Met Gly Tyr Gln His Gly Gln Leu
370                 375                 380

Thr Thr Ser Ser Gln Glu Leu Glu Arg Tyr Thr Phe Asn Pro Gln Ser
385                 390                 395                 400

Lys Cys Gly Arg Ala Pro Lys Gln Gln Phe Asn Gln Gln Ser Pro Leu
                405                 410                 415

Asn Leu Gln Asn Thr Asn Asn Gly Thr Leu Leu Pro Ser Asp Pro Ile
                420                 425                 430

Gly Gly Lys Thr Asn Met His Phe Met Asn Thr Leu Asn Thr Tyr Gly
                435                 440                 445

Pro Leu Thr Ala Leu Asn Asn Thr Ala Pro Val Phe Pro Asn Gly Gln
                450                 455                 460

Ile Trp Asp Lys Glu Leu Asp Thr Asp Leu Lys Pro Arg Leu His Val
465                 470                 475                 480

Thr Ala Pro Phe Val Cys Lys Asn Asn Pro Pro Gly Gln Leu Phe Val
                485                 490                 495

Lys Ile Ala Pro Asn Leu Thr Asp Asp Phe Asn Ala Asp Ser Pro Gln
                500                 505                 510

Gln Pro Arg Ile Ile Thr Tyr Ser Asn Phe Trp Trp Lys Gly Thr Leu
                515                 520                 525

Thr Phe Thr Ala Lys Met Arg Ser Ser Asn Met Trp Asn Pro Ile Gln
                530                 535                 540

Gln His Thr Thr Thr Ala Glu Asn Ile Gly Asn Tyr Ile Pro Thr Asn
545                 550                 555                 560
```

```
Ile Gly Gly Ile Lys Met Phe Pro Glu Tyr Ser Gln Leu Ile Pro Arg
            565                 570                 575
Lys Leu Tyr
```